United States Patent
Diaz et al.

(10) Patent No.: US 7,229,402 B2
(45) Date of Patent: *Jun. 12, 2007

(54) MINIMALLY INVASIVE VENTRICULAR ASSIST TECHNOLOGY AND METHOD

(75) Inventors: Cesar M. Diaz, Lake Forest, CA (US); Francisco Duran, Rancho Santa Margarita, CA (US)

(73) Assignee: Cardiac Output Technologies, Inc., Irvine, CA (US)

(*) Notice: Subject to any disclaimer, the term of this patent is extended or adjusted under 35 U.S.C. 154(b) by 485 days.

This patent is subject to a terminal disclaimer.

(21) Appl. No.: 10/639,103

(22) Filed: Aug. 12, 2003

(65) Prior Publication Data

US 2004/0034272 A1 Feb. 19, 2004

Related U.S. Application Data

(63) Continuation-in-part of application No. 09/780,502, filed on Feb. 9, 2001, now Pat. No. 6,666,814.

(60) Provisional application No. 60/451,005, filed on Mar. 3, 2003.

(51) Int. Cl.
*A61M 1/10* (2006.01)
*A61N 1/39* (2006.01)

(52) U.S. Cl. ............... 600/17; 607/3; 607/4; 607/5; 600/16

(58) Field of Classification Search ......... 600/16, 600/17, 18; 623/3.1, 3.11, 3.13, 3.16, 3.21, 623/3.24; 607/3, 4, 5
See application file for complete search history.

(56) References Cited

U.S. PATENT DOCUMENTS

| | | | | |
|---|---|---|---|---|
| 4,116,589 A | * | 9/1978 | Rishton | 417/384 |
| 4,459,977 A | | 7/1984 | Pizon et al. | 128/1 D |
| 4,648,384 A | * | 3/1987 | Schmukler | 600/18 |
| 4,804,358 A | | 2/1989 | Karcher et al. | 600/17 |
| 4,985,014 A | | 1/1991 | Orejola | 600/16 |
| 5,688,245 A | | 11/1997 | Runge | 604/151 |
| 6,666,814 B2 | * | 12/2003 | Downey et al. | 600/18 |

* cited by examiner

Primary Examiner—Kennedy Schaetzle
(74) Attorney, Agent, or Firm—Charles D. Gunter, Jr.

(57) ABSTRACT

The present invention is a cardiac-assist device and technique used to maintain a patient's cardiac output when normal cardiac output is insufficient. Blood is removed from a selected ventricle using an arterial or venous side approach. The use of a right side approach reduces the amount of work required and reduces the number of foreign objects present within the left side of the heart and associated blood transferring conduits. The device of the invention includes a flexible catheter positionable within the patient's body. An external assist mechanism connected to one end of the flexible catheter receives blood from the arterial circulation and includes a pumping membrane. A flexible cannula is connected for reinfusing blood. A control console is provided for alternately supplying vacuum and pressure to the pumping membrane. A synchronizing means varies inflation and deflation in synchrony with the cardiac cycle of a patient.

4 Claims, 19 Drawing Sheets

MINIMALLY INVASIVE VENTRICULAR ASSIST TECHNOLOGY AND METHOD

CROSS REFERENCE TO RELATED APPLICATIONS

This application is a continuation-in-part of prior Ser. No. 09/780,502, filed Feb. 9, 2001 now U.S. Pat. No. 6,666,814, entitled "Enhanced Intra-Aortic Balloon Assist Device". This application also claims priority from provisional application Ser. No. 60/451,005, filed Mar. 3, 2003, entitled "Minimally Invasive Ventricular Assist Device (MIVAD) Capable of Having Multiple Configurations Within a Patient's Body", by Cesar Diaz and Francisco Duran.

BACKGROUND OF THE INVENTION

1. Field of the Invention

The present invention relates generally to cardiac assist technologies which assist in maintaining a patient's cardiac output when the normal cardiac output is not sufficient to maintain an adequate pressure for supplying the patient's organs with arterial blood.

2. Description of the Prior Art

Recent statistics indicate that approximately ½ million Americans die of acute heart failure annually. Of these deaths, approximately 50% occur in spite of medical treatment (the other 50% do not reach the hospital). Although acute heart failure is presently treated with drugs and other therapy, present interventions are not sufficiently effective. As a result, additional measures are needed to help save lives of patients suffering from acute heart failure due to obstruction of the coronary vasculature or due to extensive cardiac surgery or other causes. Certain of these measures deal with varying or modulating coronary perfusion pressure according to the phases of the patient's cardiac cycle.

The coronary circulation system delivers blood to the heart muscle during the relaxation phase of cardiac contraction. During the contraction phase, pressure in the heart muscle rises and restricts coronary inflow, even though the arterial pressure rises due to cardiac ejection of blood. This elevation of coronary pressure increases the stiffness of the heart wall. With increased stiffness, the heart must expend more energy to bend the heart wall in order to eject blood. In other words, contraction of the heart against a large coronary pressure results in more "internal work" relative to the beneficial "external work" of ejecting blood from the heart chamber.

Theoretically, when the systolic coronary pressure is decreased, the heart wall becomes less stiff and can be more readily deformed during cardiac contraction. Thus, with reduced coronary pressure during the cardiac phase of contraction, the heart muscle requires less oxygen to overcome this important component of "internal" cardiac work. It is therefore often times desirable to vary or modulate coronary perfusion pressure according to the phases of a patient's cardiac cycle. Since perfusion pressure alters myocardial stiffness, changes in systolic stiffness should affect myocardial oxygen demand by changing the ratio of internal to external work. With a decreased systolic perfusion pressure, myocardial oxygen demands will be reduced, thereby permitting an increase in myocardial oxygen utilization efficiency.

A number of devices exist at the present time for varying or modulating coronary perfusion pressure. For example, the intra-aortic balloon catheter (IABC) is a commonly utilized ventricular assist device. This device is used when the patient's cardiac output is not sufficient to maintain an adequate arterial blood supply to the patient's organs. The IABC consists of an inflatable balloon attached to a catheter, which is advanced through the patient's femoral artery and into the descending aorta. Inflation and deflation of the balloon is accomplished by an external control unit synchronized with the heart beat. This unit rapidly inflates the balloon during the diastolic or resting phase of the heart cycle, and thus elevates diastolic aortic blood pressure and improves blood flow to the heart, the brain and other tissues. The balloon is rapidly deflated as the heart contracts. This action reduces the aortic blood pressure that the heart must overcome to eject blood from the left ventricle. Thus, the IABC is a ventricular assist device that also augments diastolic aortic blood pressure.

However, present IABC devices cannot sustain the circulation if the heart is severely diseased or injured, since ventricular ejection must be sufficient to keep the mean aortic blood pressure above approximately 60 mmHg. When the aortic pressure falls below this value, there is insufficient blood to fill the space around the balloon when it is deflated. In that case the wall of the aorta collapses around the deflated balloon of prior art devices, and the IABC becomes ineffective. Thus, present IABC devices can be used only in less severe cases of left ventricular failure.

Other technologies do exist that provide support for the ailing ventricles of the heart and include temporary or short term implant or pumping devices referred to in the industry as Left Ventricular Assist Devices (LVAD). These devices are designed to overcome the inherent design or physical limitations of IABC's but suffer the disadvantage of requiring very invasive surgical procedures, such as the thoracotomy, which consequently provides access to large chambers or conduits of blood within the body. The LVAD type devices also require significant surgical incisions and significant mechanical work in vital areas such as the aorta or heart chambers that may be a cause for complications or secondary events such as diminished mental acuity and cerebral injury now linked to the release of emboli into the brain.

A need therefore exists for a ventricular assist device which overcomes the various shortcomings of the prior art IABC and LVAD type devices presently in use.

A need also exists for a minimally invasive ventricular assist device which is capable of having multiple configurations within a patients body such that either left side support and/or right side support of the heart can be achieved using minimally invasive techniques. The device should be capable of providing true cardiac volumetric support and not merely act to unload the heart as in the case of IAB's. The device should function to actually displace clinically relevant blood volume like an LVAD but without the need for highly invasive surgical techniques. The result would be to provide a minimally invasive ventricular assist device.

Since clinical use of one device may be done while another device is also being used, a need exists for such an assist device which can also be used in conjunction with an intra-aortic balloon catheter IABC in a variety of clinical settings.

SUMMARY OF THE INVENTION

It is an object of the present invention is to provide a device and method which will reduce coronary pressure during the contraction phase and which will also increase coronary pressure and blood flow during the relaxation phase, when coronary flow normally nourishes the heart muscle.

Another object of the invention is to provide a device and method for increasing coronary flow during the relaxation phase of the cardiac cycle which thereby increases flow through primary as well as supplemental, i.e., collateral, blood vessels supplying tissue whose normal source of blood flow has been compromised by coronary artery disease, cardiogenic shock or other causes.

Another object of the present invention is to enhance the blood flow to the heart, brain, and other tissues under the conditions of poor heart function.

Yet another object of the present invention is to provide a means of enhancing the perfusion of other arteries such as the renal arteries and the aortic arch arteries.

These objects are achieved in the present invention by a circulatory enhancing apparatus for use in human patients to improve blood flow to other arteries continuous with the aorta of the patient. The device and method of the invention allow the removal of blood directly or indirectly from a selected ventricle using an arterial or venous side approach, thereafter providing for the direct or indirect infusion of the blood back into the circulatory system in one or more selected locations. The techniques of the invention can unload a distressed ventricle by unloading the heart muscle itself. This action is accomplished by drawing blood from a distressed ventricle or from an adjacent anatomical location that has hemodynamic impact on the distressed ventricle.

The device and method of the invention provide required cardiac assist in a novel manner that also allows existing technologies to work in conjunction with the minimally invasive techniques of the invention, if required. In one aspect, the invention utilizes a left side heart (arterial side) chamber access through the right side (venous side) of the heart. This approach reduces the amount of work required and reduces the number of foreign objects such as catheters and cannulas present within the left side of heart as well as within the various blood transferring conduits connected to left side of heart (e.g., the aorta, aortic arch, and arteries leading to extremities such as legs, arms, head, heart and renal artery). The present invention has implication for the treatment of reduced cardiac output ranging from those patients adequately served by the IAB (intra-aortic balloons) through patients requiring significant but short to medium term cardiac support, such as those patients requiring mechanical or human heart transplants that remain implanted for over 1 year. The device can also aid in expanding the clinical adoption of beating heart by-pass procedures by providing cardiac support that is sometimes required during these procedures and will reduce the risks associated with the expansion of this modern surgical technique.

In one preferred form, the device of the invention includes a flexible catheter having a length, an open interior, an exposed proximate end and a distal end positionable within the patient's body. The tube has at least one opening along the length thereof for admitting blood into the open interior after the tube has been installed within the arterial circulation. A supplemental assist mechanism is located externally of a patient's body and is connected to the proximate end of the flexible catheter. The supplemental assist mechanism is made up of a relatively rigid housing with an inlet and an outlet and with a housing interior in communication with the flexible catheter for receiving blood from the arterial circulation. The rigid housing also has a pumping membrane located within the housing interior. A flexible cannula is connected to the outlet of the rigid housing and has a distal end with an end opening forming a reinfusion port which is positionable within the patient's body for reinfusing blood at a desired location. A control console is provided having at least two independent control channels for alternately supplying vacuum and pressure to the pumping membrane. The application of vacuum to the membrane causes the membrane to collapse and causes blood to be drawn into the housing interior. The application of pressure to the membrane causes the membrane to inflate and act against blood in the housing interior to drive blood from the housing interior into the body of the patient. A synchronizing means, provided as a part of the control console, varies the membrane inflation and deflation in synchrony with the cardiac cycle of a patient being treated with the device.

A flexible tube is preferably connected to the control console and terminates in an intra-aortic balloon which is positionable within the patient's body at a location above the reinfusion port of the flexible cannula. The balloon is alternately inflatable and deflatable by a pressurization means provided as a part of the control console. In one embodiment of the invention, the pressurization means comprises a centrifugal or vane pump capable of providing quasi-pulsatile or pulsatile pumping action. In another embodiment of the invention, the pressurization means comprises a peristaltic pump capable of providing quasi-pulsatile or pulsatile pumping action.

In yet another embodiment of the invention, a pacing/cardioversion catheter is placed within the coronary sinus and extends into a cardiac vein for electrical stimulation or cardioversion of the left or right ventricle by applying a pacing or cardioversion pulse between the catheter in the cardiac vein and a cutaneous patch or patches or an additional catheter residing in the right ventricle. The catheter in the right ventricle or cardiac vein (or combination of both) have the ability to set the pace of heart rate such that by using the fully integrated MIVAT system, the electrical pulses also synchronize the blood pumping action, thereby rendering complete cardiac output control. By this means there is provided a system for managing one of the most complex problems in cardiac assists today, arrhythmia caused by electrical disturbances.

In yet another embodiment of the invention, a pacing/cardioversion capability has been incorporated into the tube (sheath) that is used to withdraw blood from the atria or give access to the left chambers of the heart using a transeptal puncture approach. The modified sheath has the ability to deliver or receive electrical impulses by using a conductive material ideally suited for sensing and or cardioversion (defibrillation). The electrically active region provided by the conductive material is preferably disposed in an area of the tube (sheath) that resides in the atria and/or slightly into the superior vena cava. In this way, a pulse can be established between the electrically active region in the right atrium and a cutaneous patch or patches located in a posterior or anterior position or an additional catheter positioned to provide for an electromagnetic field path through the atria. The design allows for the sheath to be mechanically connected directly or indirectly to a control console for purposes of coupling to a pumping means of the control console and/or electrical stimulation capability as discussed above.

In the preferred method of the invention, a minimally invasive technique is provided for improving blood flow in a patient's body by removing blood directly or indirectly from a selected ventricle or other selected region of the heart and then directly or indirectly infusing the blood back into the patient's circulatory system at a selected distant location. As a first step in the technique, a flexible catheter, as previously described, is installed within a selected side of the patient's heart. The flexible catheter has an infusion opening for admitting blood into the open interior after the catheter has been installed within the arterial circulation. A supplemental assist mechanism is located externally of a patient's body and connected to a proximate end of the flexible catheter. The supplemental assist mechanism includes the rigid housing with an inlet, an outlet, and with a housing interior in communication with the flexible catheter for receiving blood from the arterial circulation, as previously described. The rigid housing also has a pumping membrane located within the housing interior. A flexible cannula is connected to the outlet of the rigid housing. The cannula has a distal end with an end opening forming a reinfusion port which is located within the patient's body at the selected distant location. A control console is also provided, as previously described for alternately supplying pressure and vacuum to the pumping membrane.

A synchronizing means, provided as a part of the control console, is provided for varying the membrane inflation and deflation in synchrony with the cardiac cycle of a patient being treated with the device. In a particularly preferred technique of the invention, the flexible catheter is placed into the right atria of the heart, access to the left atria being gained by means of a transeptal puncture of the atrial septum wall of the patient's heart and the open lumen or lumens being in direct contact with the arterial blood contained in the left atria. A particularly preferred location for reinfusing blood into the patient's circulatory system is the lower aorta of the patient well below the aortic arch, closer in proximity to the femoral artery bifurcation with the patient's aorta. In a particularly preferred technique using the device of the invention, a flexible tube is connected to the control console which terminates in an intra-aortic balloon. The balloon is positioned within the patient's body at a location above the reinfusion port of the flexible cannula and can be alternately inflated and deflated. The pump means used on the reinfusion cannula can be pulsatile, quasi-pulsatile or non-pulsatile. The IAB, by its very nature of inflating and deflating in synchrony with the pumping apparatus, can therefore generate part of the pulsatile pressure wave that is required to prevent blood clotting around the heart valves and to prevent the formation of low turbulence regions of anatomy. The combination device can also utilize a reduced size IAB in comparison to those used in similar sized patients today, since it will aid in the assist process by providing the only true physiological effects the IAB delivers; unloading the ventricle during systole and creating hydroshock by rapidly inflating during diastole.

In another preferred technique of the invention, a coronary sinus cannula is connected to the outlet of the rigid housing, the coronary sinus cannula being positionable within the right side of the patient's heart. An additional control console can also be connected to an intra-aortic balloon which is positionable at a location in the patient's body above the reinfusion port of the flexible cannula.

In another embodiment of the method of the invention, the flexible catheter includes a transeptal cannula which is advanced through a heart valve into the left ventricle of the patient, the transeptal cannula carrying a retaining balloon for maintaining the position of the cannula in the left ventricle.

The pressurization means which is provided as a part of the control console is preferably capable of providing either quasi-pulsatile or pulsatile pumping action. This can be accomplished by using any of a number of conventional pumping devices, including centrifugal or vane pumps or peristaltic pumps.

Additional objects, features and advantages will be apparent in the written description which follows.

DETAILED DESCRIPTION OF THE INVENTION

Figure 1:
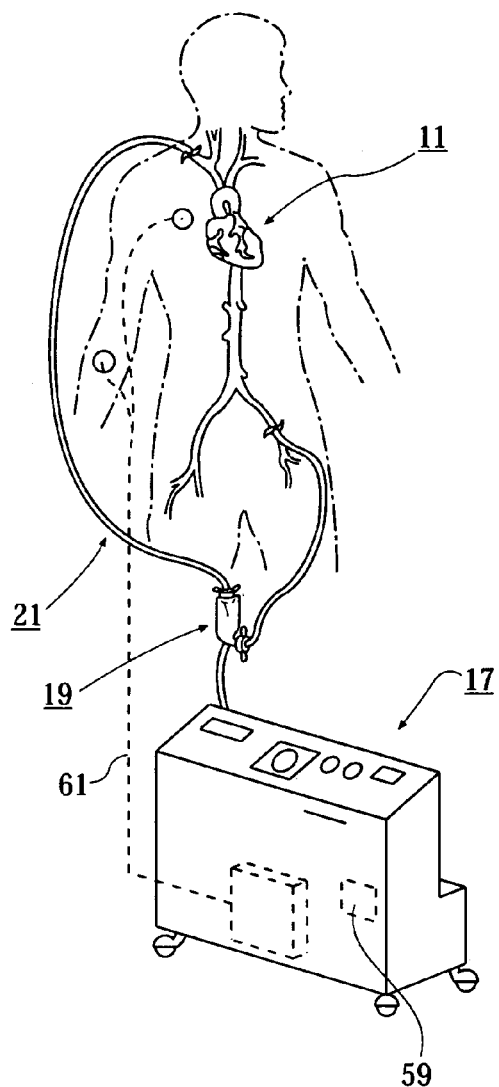
FIG. 1 is a simplified view of the human anatomy showing portions of the arterial circulation and showing the external pump and synchronizer used with the device of the invention.

APPARATUS. The term "MIVAT" (Minimally Invasive Ventricular Assist Technology) will be used in the discussion which follows to describe a preferred system of the invention which includes a control console with at least two independent control channels controlled by computer or other electronic means. The independent (optionally synchronizable) channels are those required to inflate or deflate pumping devices of the invention including catheters or cannulas described herein as the SAM-CS (Supplemental Assist Mechanism and Catheter System). The control console includes a pneumatic control system which can be used to drive and control a gas powered rotary motor that can be designed to create a quasi-pulsatile pumping action because it draws or pumps blood in synchronized action with the hearts systolic/diastolic pumping process. The system can optionally be equipped with an electric motor control module or modules having speed and torque control and/or an engineering unit feedback control loop, as will be familiar to those skilled in the art. The motor control system can also be designed to create a quasi-pulsatile pumping action because it draws or pumps blood in synchronized action with the hearts systolic/diastolic pumping process. The use of a peristaltic pump head or a centrifugal pump can be used to create the quasi-pulsatile pump action, allowing some amount of continuous flow at all times. The MIVAT system which is to be described inherently has the ability to drive both novel devices such as the SAM-CS or to drive standard IABC type devices.

The MIVAT control console, in one preferred form, comprises a data acquisition and control center for the management of patient cardiac output. In addition to supporting both the SAM-CS and standard IAB (cardiac assist devices), the MIVAT control console can gather hemodynamic function data, induce and or terminate arrhythmia using low voltage pacing trains (as known in the art) and gather multiple electrical signals from inside the heart chambers using standard and or novel products routinely used by electrophysiologists. The MIVAT is the control center for management of acute and short-term chronic hemodynamic deficiencies of the heart that cause the patient to present to the hospital or other emergency center. The ability to gather electromechanical data into a single or linked computational center and to display that data in an integrated display provides physicians with an ideal tool to diagnose, monitor and also treat acute "electromechanical" events which have hemodynamic implications to patients. The diagnostic capability of the MIVAT system also makes the platform ideal as a diagnostic center for managing the implantation of ICD (Implantable Cardioverting Defibrillators) and or pacemakers that are intended to address deficiencies of cardiac output due to heart failure or arrhythmia.

The apparatus of the invention will first be described with reference to FIGS. 1 and 2. FIG. 2 is a simplified, isolated view of a human heart 11 with its coronary blood supply. The main coronary arteries 13, 15 lie on the surface of the heart while the smaller arteries 16 penetrate from the surface into the cardiac muscle mass. These arteries supply the heart with the majority of its nutritive blood supply since approximately only the inner 75–100 micrometers of the endocardial surface can obtain significant amounts of nutrient directly from the blood in the cardiac chambers.

The left coronary artery 13 supplies mainly the anterior and lateral portions of the left ventricle. The right coronary artery 15 supplies most of the right ventricle as well as the posterior part of the left ventricle in about 80 to 90% of all persons. Most of the venous blood flow from the left ventricle leaves by way of the coronary sinus (not shown) which is about 75% of the total coronary blood flow while most of the venous blood from the right ventricle flows through the small anterior cardiac veins directly into the right atrium, not by way of the coronary sinus. The resting coronary blood flow in the human averages about 225 ml/min, which is about 0.7 to 0.8 ml per gram of heart muscle, or about to 5% of the total cardiac output.

Figure 2:
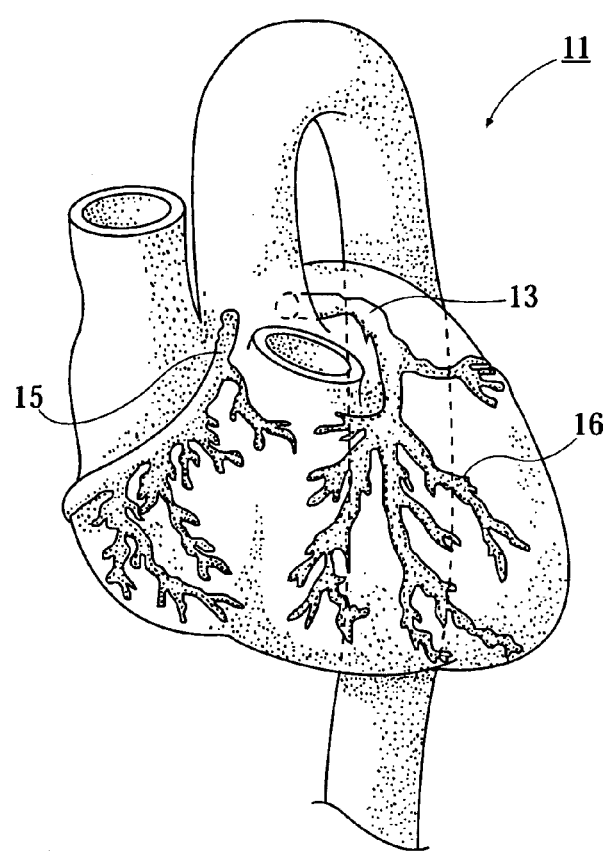
FIG. 2 is a simplified, isolated view of the human heart with its coronary blood supply.
Figure 3:
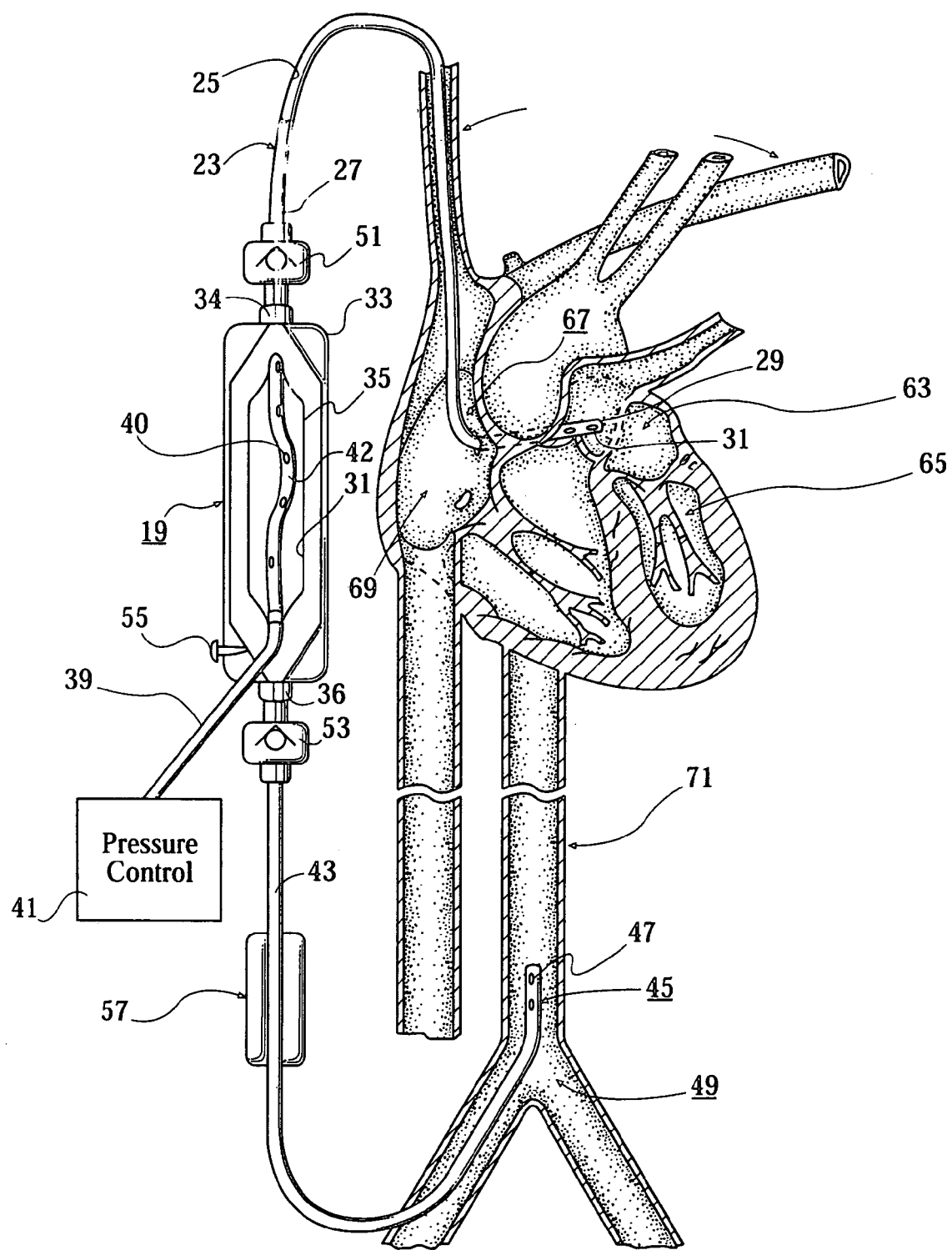
FIG. 3 is a simplified, partly schematic view of a portion of the heart and coronary artery of the heart with the device of the invention installed such that the left heart chambers are accessed from the right side.

FIG. 1 is a simplified illustration, partly schematic, of the MIVAT system of the invention. The system includes a control console 17, a supplemental assist module (SAM) 19, and one or more catheter systems (CS) 21. FIG. 3 shows the MIVAT and SAM systems in greater detail. As shown in FIG. 3, the systems include a flexible catheter 23 having a length, an open interior 25, an exposed proximate end 27 and a distal end 29 positionable within the patient's body. The catheter 23 has at least one opening 31 along the length of the flexible catheter for admitting blood into the open interior 25 after the catheter has been installed within the arterial circulation.

The supplemental assist mechanism (SAM) 19 which is located externally of the patient's body is connected to the proximate end 27 of the flexible catheter 23. As shown in FIG. 3, the SAM preferably comprises a relatively rigid, elongate housing 33 having an inlet 34 and an outlet 36 and with a housing interior 39 in communication with the flexible catheter 23 for receiving blood from the arterial circulation. By "relatively rigid" housing is meant that the housing 33 is formed of a rigid or semi-rigid construction, whereby the housing is capable of being used both as a pressure chamber and as a vacuum chamber. The rigid housing 33 also has a pumping membrane 35, in this case an inflatable balloon, contained within the interior 37 thereof. The membrane 35 extends lengthwise within the housing interior 37 and has a trailing extent 39 which is connected to a pressurization means 41 provided as a part of the control console 17. The trailing extent 39 communicates with openings 40 provided in an internal lumen 42 for alternately applying either vacuum or pressure to the pumping membrane 35.

A flexible cannula 43 is connected to the outlet 36 of the rigid housing 33. The cannula 43 has a distal end 45 with one or more end openings 47 forming a reinfusion port which is positionable within the patient's body for reinfusing blood at a desired location. In the example shown in FIG. 3, the reinfusion port 47 is located well below the aortic arch, in closer proximity to the femoral artery bifurcation 49 with the patient's aorta.

The SAM also includes upper and lower check valves 51, 53 which control the flow of blood into and out of the rigid housing 33. Check valve 51 opens under vacuum and closes under pressure. Similarly, check valve 53 closes under vacuum but opens under pressure. Check valve 51 thus allows blood flow into the housing interior 37 but closes under pressure so that the blood passing through the valve cannot return in the direction of the ventricle. As will be explained more fully, gas pressure and vacuum are alternately applied through the member 39 to the pumping membrane 35 to inflate and deflate the membrane 35. Check valve 53 opens under the presence of pressure, allowing fluid ejection through the housing outlet 36 in the direction of the femoral bifurcation 49 or other desired location.

The pumping process is facilitated by choosing a balloon or membrane material for use in the external SAM-CS pumping chamber and/or internal balloons (or IAB) used as a part of the catheter system (CS) which has sufficient elastic recoil. The elastic modulus for the pumping membrane or balloon is ideally specified such that when the polymer is over extended or elongated and then released the polymer actually recovers or recoils quickly, causing rapid reduction in volume and therefore increased pressure within the balloon or membrane. This recoil action causes the balloon or membrane to actually self-vent gas until it reaches equilibrium with the surrounding region or apparatus until subsequent application of vacuum in the pressurization/vacuum cycle collapses the balloon or membrane. The ideal material properties of the balloon or membrane for purposes of the present invention are given as follows:

Tensile modulus at 50%=from 600 psi to 2400 psi;
Tensile modulus at 100%=from 800 psi to 3000 psi;
Ultimate Tensile at break=over 3000 psi; and
Ultimate elongation over 200%

In the embodiment of the invention illustrated in FIG. 3, the rigid housing 33 also has an auxiliary IV connection or port 55 which can be utilized for injecting drugs or other agents into the blood stream of the patient. An auxiliary blood treatment system 57 can also be present in the system of the invention. Thus, instead of utilizing a simple IV connection, the pressurized blood can be directed to the filtering components of a blood treatment system, for example for hemodialysis. If desired, the blood could be oxygenated at this point in the system by providing the appropriate oxygenation equipment.

The control console 17 includes a pressurizing means, such as pump 59 in FIG. 1, provided as a part of a synchronizing means, the pump communicating with the housing interior 37 by means of the member 39. The pump 59 is used to supply a pressurized gas, such as helium, to the lumen 42 of the inflatable membrane 35. The synchronizing means, provided as a part of the control console 17, varies the balloon inflation and deflation states in synchrony with a cardiac cycle of the patient being treated with the device. Various pump devices of this general type, as well as associated synchronizing means, have been commercially available as a combined unit and have been used for many years in patients which cardiogenic shock. Any suitable commercially available device can be utilized for varying the pressure in the balloon 35 in synchrony with a desired cardiac cycle may find application for purposes of the present invention. In addition to monitoring such parameters as the coronary pressure, additional input (61 in FIG. 1) from such sources as an electrocardiogram of the patient will be used to control the synchronizer.

As previously mentioned, the MIVAT system of the invention preferably utilizes a control console having at least two independent control channels for alternately supplying vacuum and pressure to the pumping membrane 35. The control channels are triggered by specific events related to the QRS complex of heart function. It is not necessary that the triggering event be tied to the "R" event and, in fact, any event in the QRS complex can be utilized. The control channels for the pressurization means are preferably designed for independent control to allow different pressures and flow rates for the intended application.

The control console may utilize a dual pump arrangement, the dual pumps being independently adjustable and operable, or the pumps could also be synchronized to augment and supplement the heart action, as well. Also, although a dual stage pump assembly may be envisioned, multiple stage pump assemblies are also envisioned with the pump stages operating either in sequence or out of sequence, the pumps being independently adjustable and operable based upon one biological model obtained through the ECG and QRS complex of the patient.

The preferred pressurization means of the invention includes a pumping sub-system having a control system capable of sensing the function of the heart via electrical, pressure signals and or combination of both. The system then has the ability to move blood from one location in the body to another via a pulsatile or quasi pulsatile flow mechanism that is connected to specialized catheters and or cannulas located in desired locations of the body. In a particularly preferred form of the invention, a pump present as a part of the control console 17 includes at least two separate control channels for at least two separate devices or one device with multiple functions. The pressurization means further comprises means by which analog and or digital signals are processed to manage the proper sequence of each device and the inter-relationship of all devices connected to the MIVAT system and their proper function so as to be synchronized or non-disruptive of the heart's function.

A particularly preferred pressurization means incorporates a pneumatic drive system which is designed to overcome the physical limitations of vacuum by utilizing to its advantage the use of pressure. The system is referred to herein in terms of a method and apparatus which utilize a "Snap-Crackle-Puff" valving sequence which is used to manage the vacuum/pressure cycle of the system. The Snap-cycle is used to optimize the vacuum cycle by use of valve sequences that optimize use of pressure cycle to help assist the deflation (vacuum) cycle.

OPERATION. The preferred Snap-Crackle-Puff valving process will now be described. In the first step in the process, "Snap", vacuum (negative pressure) is applied to the pumping chamber of MIVAT or IAB when a valve opens to the chamber under stored vacuum. The balloon or pumping membrane is deflated in a snap because the gas or air in balloon (membrane) is removed, allowing the pumping balloon (membrane) to collapse upon itself. The vacuum (negative pressure) is the maximum that can be generated at varying altitudes from sea level by a vacuum pump, diagram or other mechanism know in the art that can generate negative pressure but whose physical size, construction and function are adequate for the fully functioning apparatus.

The next step in the process is "Crackle", the process of cracking open the pressure valve connected to the pressurized vessel and/or gas source. The pressure is controlled through at least one pressure regulator or a set of staged regulators, depending upon the level of pressurization of the source or that required for safety. The balloon or membrane therefore inflates rapidly and when doing so acts against the blood or fluid within the pumping chamber so that the reduction of space within the rigid housing or pumping chamber is rapidly reduced by the inflation of balloon. This pressure is sufficient to drive the optimum amount of blood from pumping chamber into the patient during diastole or more rapidly if required.

The final step in the process is that described as "Puff" or venting of compressed gas to the atmosphere (other atmospheric pressure vessel, filtering or staging chamber) which was used to inflate the balloon (normally during start or just before systole). The act of opening the valve to allow the compressed gas to rush out reduces the number of molecules that the vacuum side of system needs to remove to deflate the balloon (membrane). This allows the vacuum pump, diaphragm or other mechanism to be reduced in size or for its efficiency to be increased.

The process then returns to the "Snap" stage, whereby the vacuum completes the job of fully deflating the balloon or membrane.

The Snap-Crackle-Puff process provides several special considerations and functional aspects or advantages which are related to cardiac assist. The Puff/Snap combination is used to deflate the balloon (start of fully primed and fluid filled external chamber or fully deflated intra-aortic balloon). The deflation causes the blood within aorta or other body lumen to drop in pressure because of a reduction in volume due to the collapse of balloon. In the case of an external chamber, the cannula or catheter connecting external chamber to the blood pool within the body causes the blood to be drawn from the body and into the housing of external pumping chamber. The removal of fluid from the aorta would have the net effect of reducing the load the left or right ventricle would have to pump against and therefore acts as a cardiac assist device similar to IAB (intra-aortic balloon). The absence of large surface area balloon and resultant turbulence near the aortic walls is reduced or eliminated and may contribute to a reduction or elimination of cardiac assist caused aneurysms and emboli. The "Crackle" stage is used to inflate the balloon and thus moves or pumps blood from an external reservoir or within body lumen to another location by displacing blood.

The inflation and deflation of the balloon is sequenced with the EKG or pressure wave created with normal function of the heart, the electrical signal being that best characterized by the QR complex. A pressure wave is generated in various parts of the body but more specifically the aorta, left ventricle or atrium or right ventricle or atrium, whereby the pressure can be measured using a highly sensitive pressure probe. Pressure probes are known in the art of sensing and include fluid columns, fiber optics, solid state sensors or other sensor technologies. The pressure wave so produced is characterized and possibly digitized so that sequencing of the pumping action of the MIVAT system can be done with corresponding cardiac cycle. The use of a pressure sensor also allows for valve closures to be detected and used to predict the next cardiac event. The notch caused by fast flow change due to closing of heart valves and the resultant pressure change can be used to predict the next "R" peak or other portions of the QRS complex, depending on location of pressure sensor within the patient.

One important aspect of the present invention involves the combined use of electrical and pressure measurements to monitor the function of the heart and also to time the proper cycling of the MIVAT and or IAB with the realization that can both be connected to the control console, allowing for multiple treatment options to be created. The timing of proper inflation and or deflation of each device can be independently controlled yet integrated through the cardiac monitoring system that is part of control console. The single source data collection center (a computer within the control console), permits the creation of algorithms used to plan the treatment sequence for each cardiac support mechanism and also to control the amount of resulting affect each will have. The ability to gradually reduce the cardiac assist function can be beneficial in weaning the patient off support. The infusion of blood can be preferential and infusion of large amounts of blood and or other critical fluids into the patients head and heart to sustain life or address acute heart failure or cardiogenic shock event is another key aspect of the integrated support system approach. The preferential sequence can also be used to protect against renal failure and or preserve limbs once the patients life is saved by heavy perfusion of renal artery limbs to ensure irreparable harm is not caused.

The control console of the MIVAT system may also be equipped with an on board pacer for ventricular or atrial pacing of one to four heart chambers. The control console may also be optionally equipped with an on board defibrillator for low-energy or high-energy defibrillation. The process of pumping blood in synchrony with heart beat or pacing the heart or defibrillating the heart in synchrony is preferably achieved through the on board signal processor. The source of external ECG signals can be external or intercavitary signals attained, e.g., by the use of an indwelling catheter, located in the right ventricle with a tip and at least one ring electrode.

OTHER CONFIGURATIONS. FIGS. 3–18 attached show some, but not all, of the additional possible configuration that can be achieved using the MIVAT system. While the illustrated configurations are intended to be illustrative of various additional aspects of the invention, they are not intended to be limiting of the scope thereof. Additional modifications which come within the scope of the present invention will be apparent to those skilled in the relevant arts.

First again having reference to FIG. 3 of the drawings there is shown the Supplemental Assist Module and Catheter System (SAM-CS) in a "least aorta disruptive" placement such that the left heart chambers (arterial side) including the left atrium 63 and left ventricle 65 are accessed from the right side (venous side) by means of a transeptal puncture 67 of the right atrium 69. The cannula through the atrial septum wall draws blood out of the left atrium 63 and then reinfuses that blood back into the lower aorta 71 by means of the previously described cannula 43 with its reinfusion ports 47. This technique allows for work to occur well below the aortic arch and closer to the femoral artery bifurcation 49 with aorta. The catheter tip 29 passing through atrial wall can be equipped with a balloon or other mechanical means of retaining the cannula in place during use. The cannula tip 45 within aorta can be equipped with small cuffing balloon such that the blood flow is occluded temporarily and preferential flow toward upper extremities is promoted.

Figure 4:
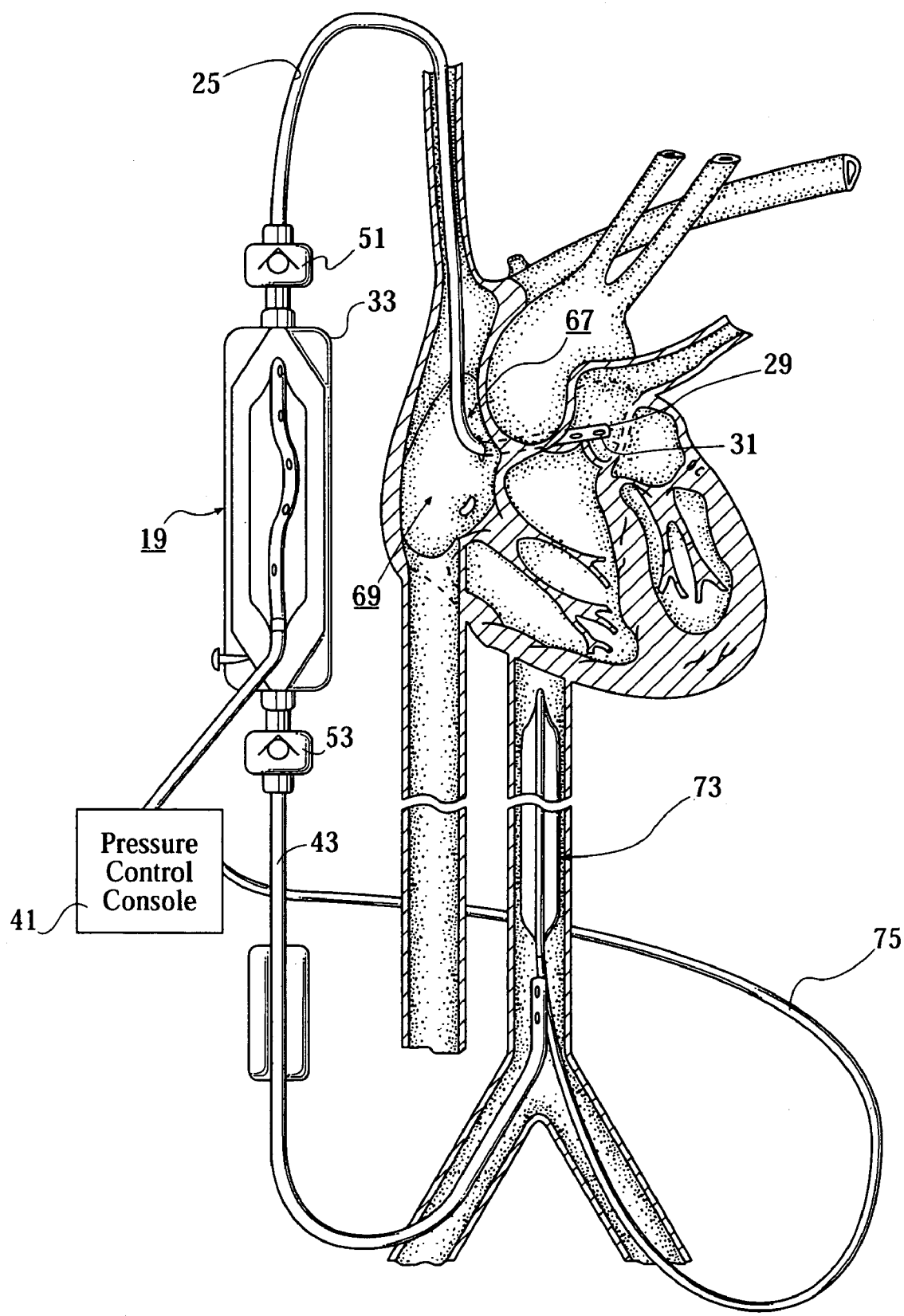
FIG. 4 is a view similar to FIG. 3 except that an intra-aortic balloon is also used and coupled to a pressure control console.
Figure 5:
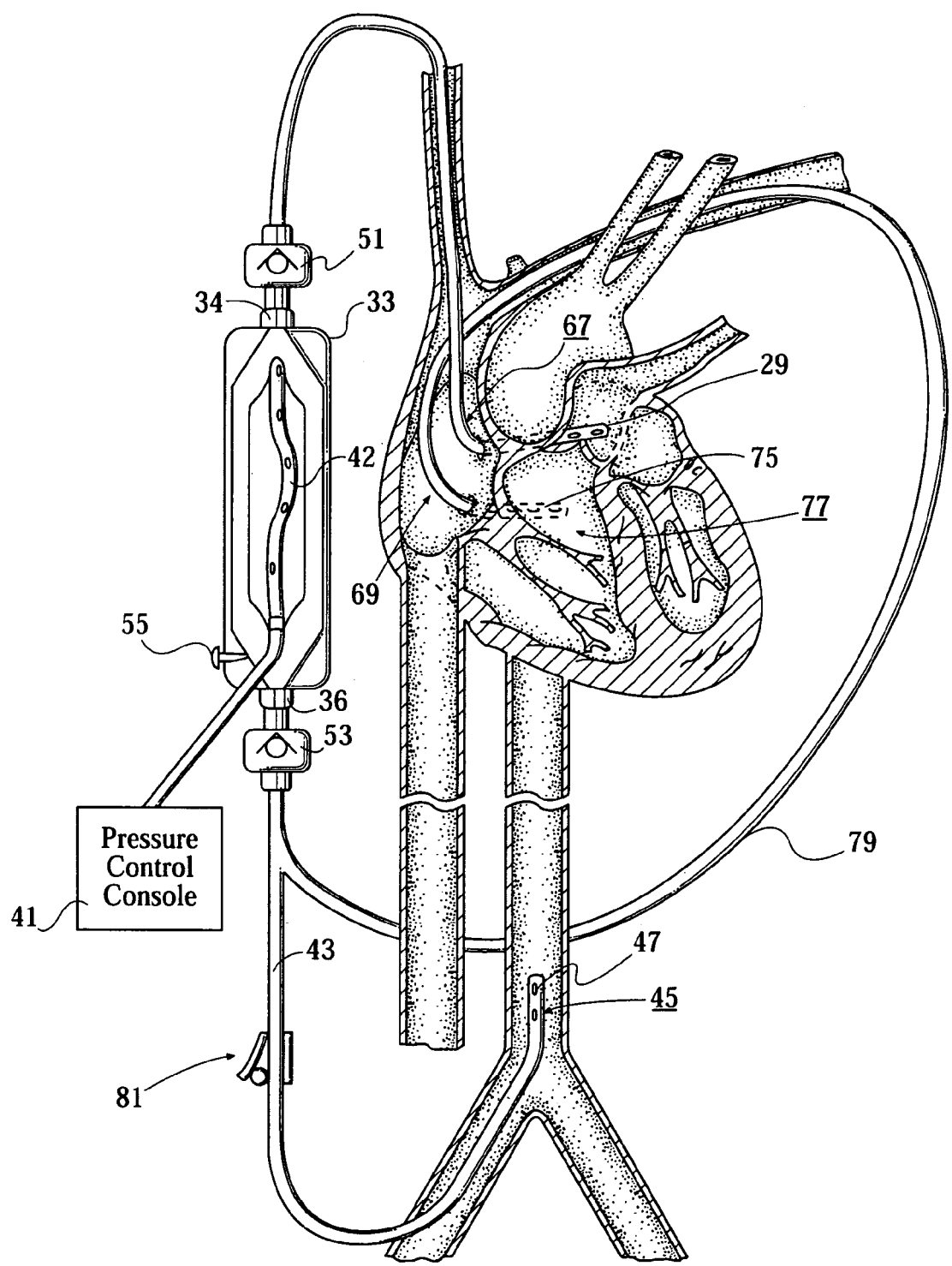
FIG. 5 is another view of the device of the invention with an additional cannula introduced into the coronary sinus and coupled to the external pressure console.

FIG. 4 is similar to FIG. 3 but also shows an intra-aortic balloon 73 which is coupled to the MIVAT console 41 by means of the flexible tube 75. The singular control console allows for accurate sychronization of the various devices to the heart's normal pumping action using standard electrical or pressure inputs.

FIG. 5 is again similar to FIGS. 3 and 4 except that an additional catheter 75 is introduced into the coronary sinus 77 and is coupled to the MIVAT console by means of the flexible tube 79. The coronary sinus catheter 75 allows for retroperfusion of the myocardium through the veins branching from the coronas sinus. The blood will be infused into the coronary sinus during the filling phase of the ventricle which promotes the retrograde perfusion of the myocardium. However, a pulse of blood must be used to ensure that the capillary bed is expanded just enough so that perfusion of the heart muscle can occur. The coronary sinus catheter 75 can also be provided with an integrated cuffing balloon to block and preferentially force flow into capillary bed of the ventricles. The coronary sinus catheter 75 can also optionally be equipped with single or multiple electrodes that allow for electrical sensing, electrical stimulation or cardioversion of the heart by use of other catheters or cutaneous surface electrodes that are properly located within the hearts chambers on the same catheter. Note that the flexible cannula 43 is also equipped with a flow adjustment mechanism 81.

Figure 6:
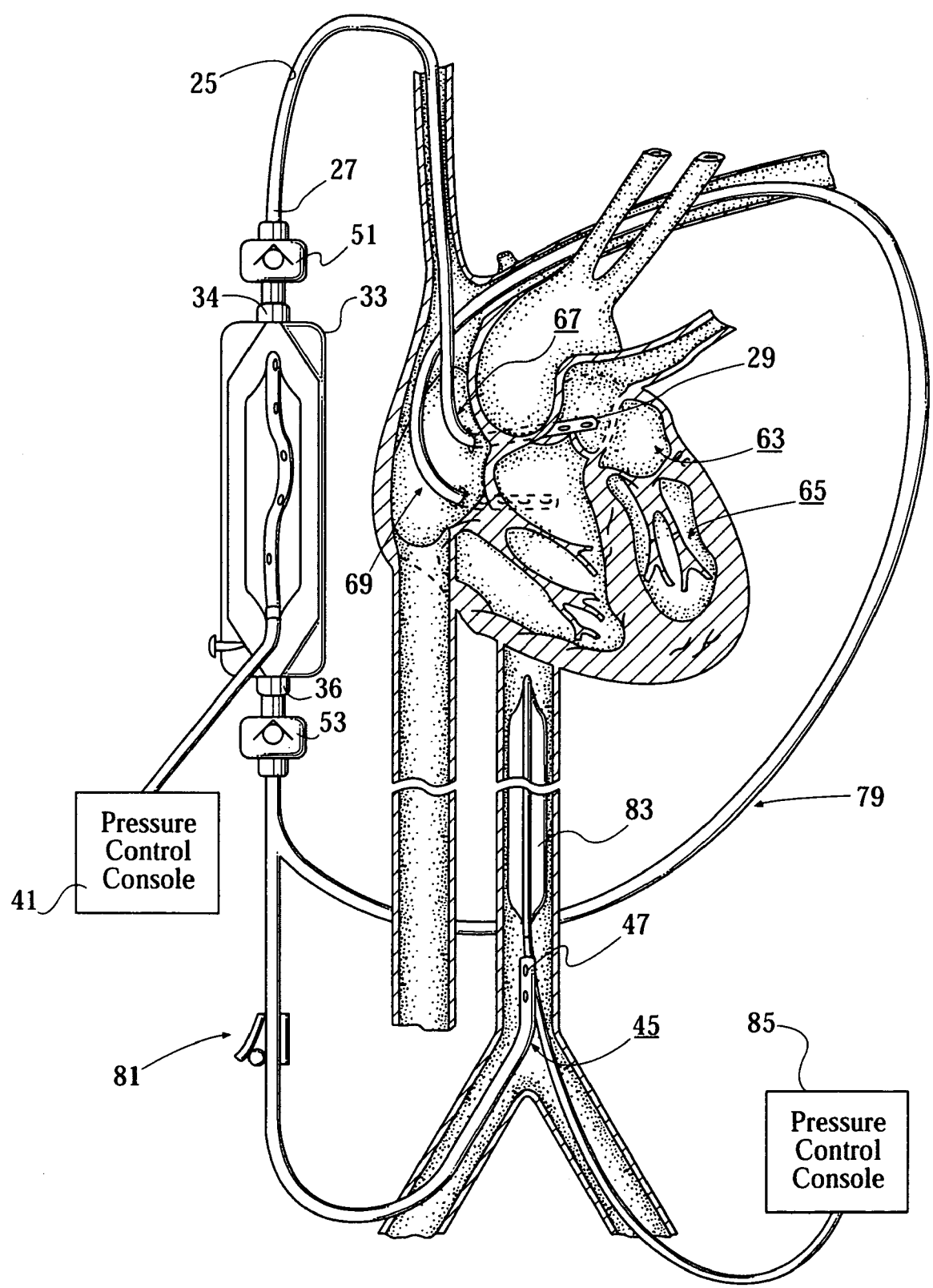
FIG. 6 is a view of the device of the invention, similar to FIG. 5, but with an intro-aortic balloon also being used.

FIG. 6 is similar to FIG. 3 except that an intra-aortic balloon 83 is also used and coupled a MIVAT console. In this case a separate control console 85 is utilized. The control console allows for accurate sychronization of the devices to the heart's normal pumping action using standard electrical or pressure inputs. Sychronization of the electrical stimulation or cardioversion of the heart and pumping action of the pumping mechanism can be fully integrated and managed with the MIVAT control console to ensure that complete electro-mechanical integration and management can occur. The data that is gathered from the devices is then fed into central processor of the MIVAT console with proper algorhythms used to manage multiple device interactions and proper treatment regiments.

Figure 7:
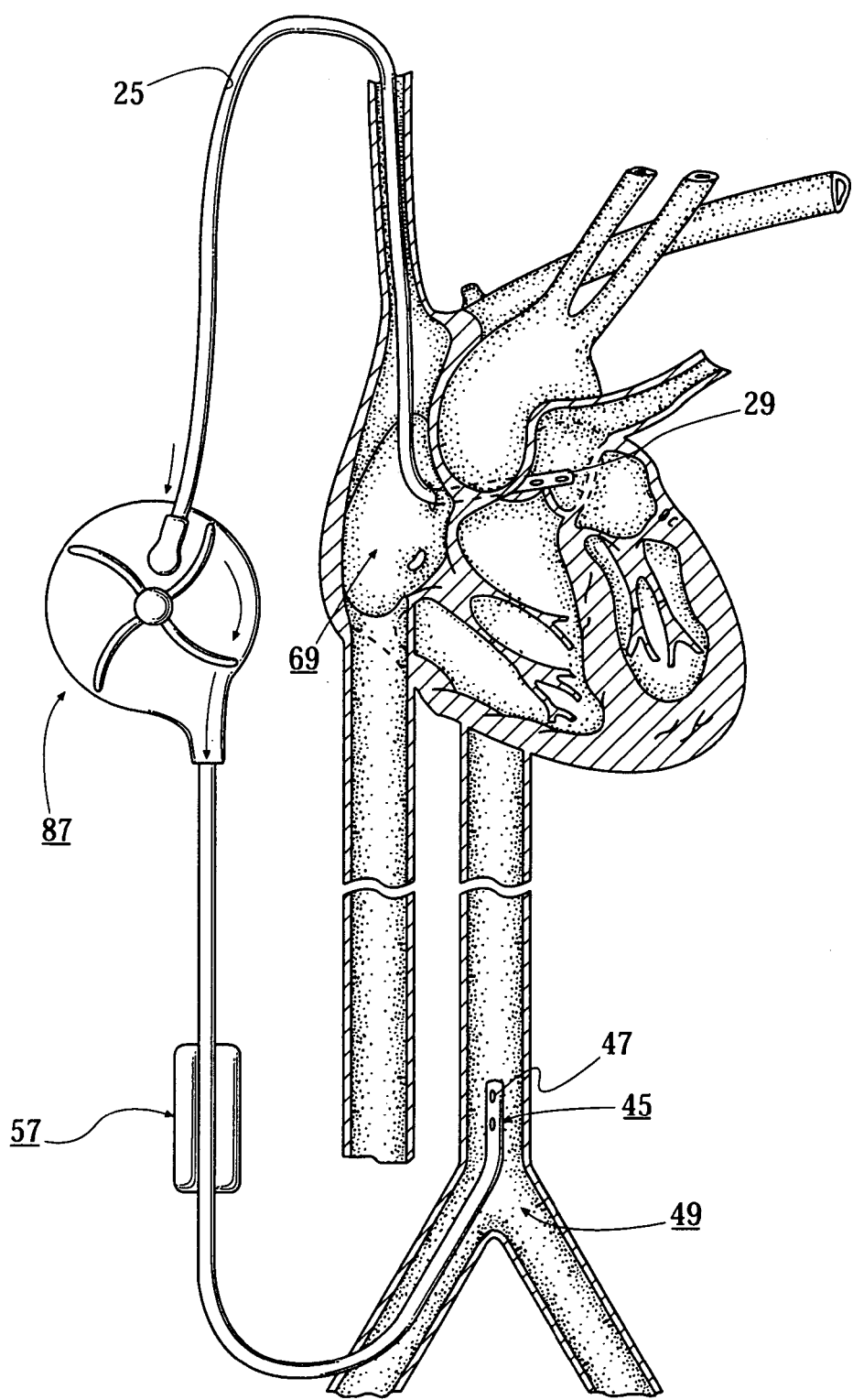
FIG. 7 is another view of the device of the invention in which a centrifugal pump is used for continuous flow.

FIG. 7 again shows a Supplemental Assist Module and Catheter System (SAM-CS) of the invention in a "least aorta disruptive" placement such that the left heart chambers (arterial side) are accessed from the right side (venous side). The cannula through the atrial septum wall draws blood out of the left atrium and then reinfuses that blood back into the lower aorta. In the embodiment of FIG. 7, a centrifugal pump 87 is used for maintaining continuous flow. The centrifugal pump 87 can also be equipped with solenoid valves that are used to build pressure and then open fully (always partially open to ensure no stagnation of blood occurs) and yet closing to low volume flow quickly to create a continuous yet quasi-pulsatile flow pulse of blood. The quasi-pulsatile design allows for higher volume per minute to be achieved yet provides the very important pressure gradient changes or hydroshock that are required to properly perfuse the heart capillary bed and promote gas exchange in body tissues. In this regard, note that the apparatus of FIGS. 3–6 inherently are pulsatile.

Figure 8:
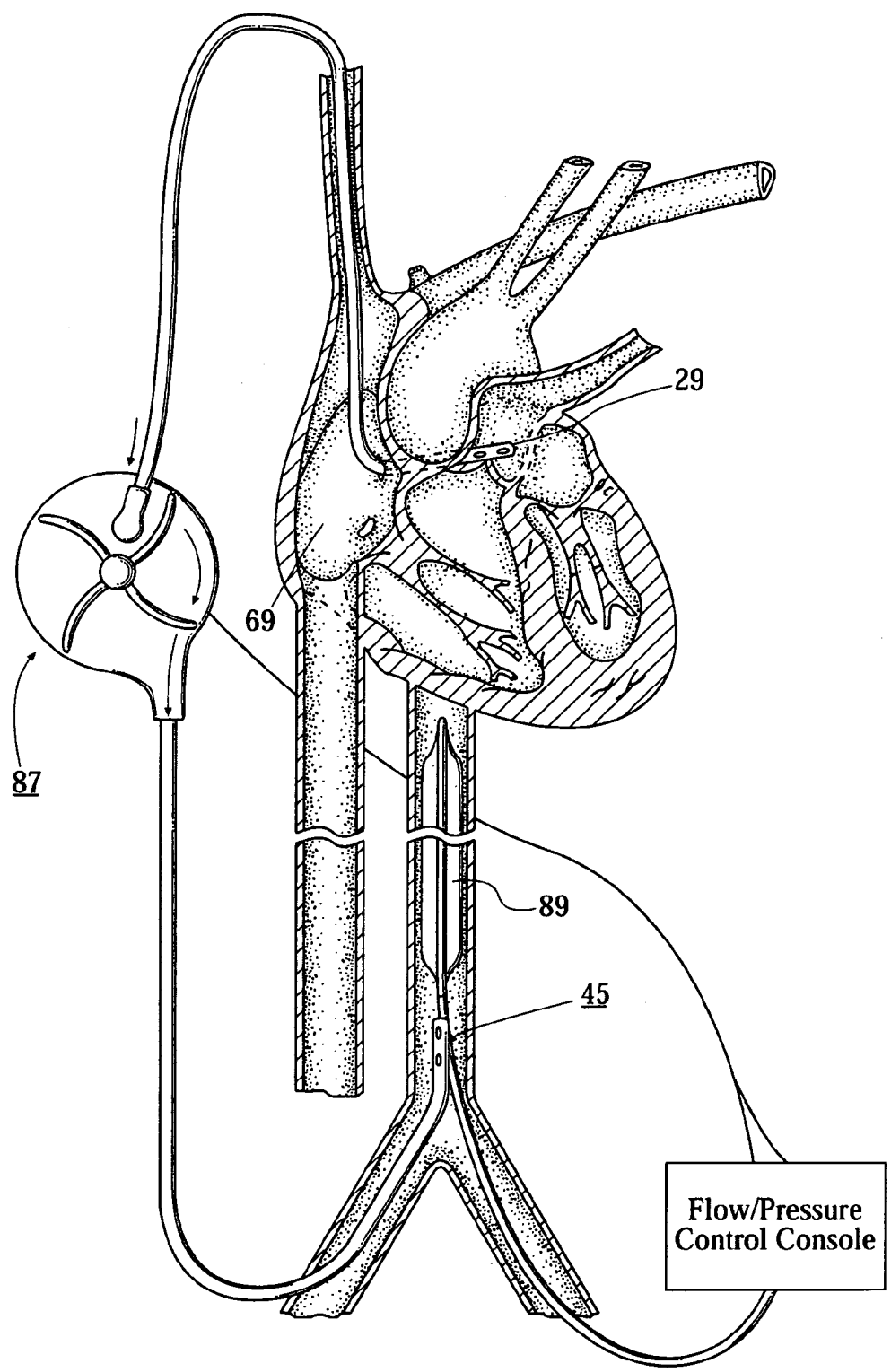
FIG. 8 is a view similar to FIG. 7 but showing an intra-aortic balloon also being present and coupled to the external pressure console.

The arrangement illustrated in FIG. 8 is similar to that shown in FIG. 7 except that an intra-aortic balloon 89 is also used and coupled to a MIVAT console 91. The singular control console 91 allows for accurate sychronization of the devices to the heart's normal pumping action using standard electrical or pressure inputs.

Figure 9:
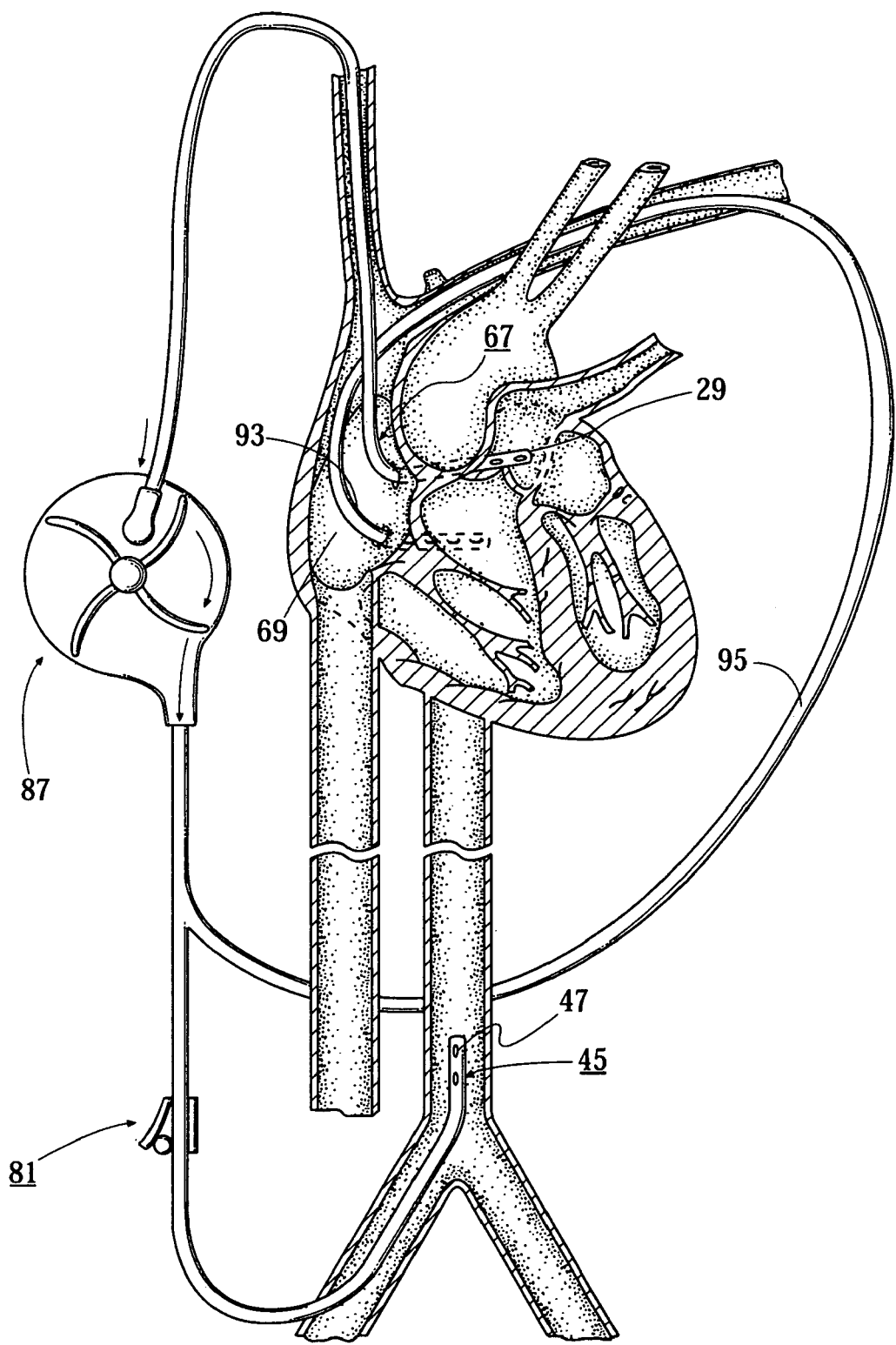
FIG. 9 is a view similar to FIG. 6 except that an additional cannula is introduced into the coronary sinus.

FIG. 9 is similar to FIG. 8 but shows an additional cannula 93 is introduced into the coronary sinus and fed from the pump 87 and flexible tube 95. The coronary sinus placement of the device allows for retroperfusion of the myocardium through the veins branching from the coronary sinus. The blood will be infused into coronary sinus during the filling phase of the ventricle which action promotes the retrograde perfusion of the myocardium. As stated previously, however, a pulse of blood must be used to ensure that the heart capillary bed is expanded just enough so that perfusion of the heart muscle can occur. The coronary sinus catheter can be equipped with an integrated cuffing balloon to block and preferentially force flow into the capillary bed of ventricles. The coronary sinus catheter can also be equipped with an optional single or multiple electrodes that allow for electrical sensing, electrical stimulation or cardioversion of the heart by use of other catheters or cutaneous surface electrodes that are properly located within the hearts chambers on the same catheter.

Figure 10:
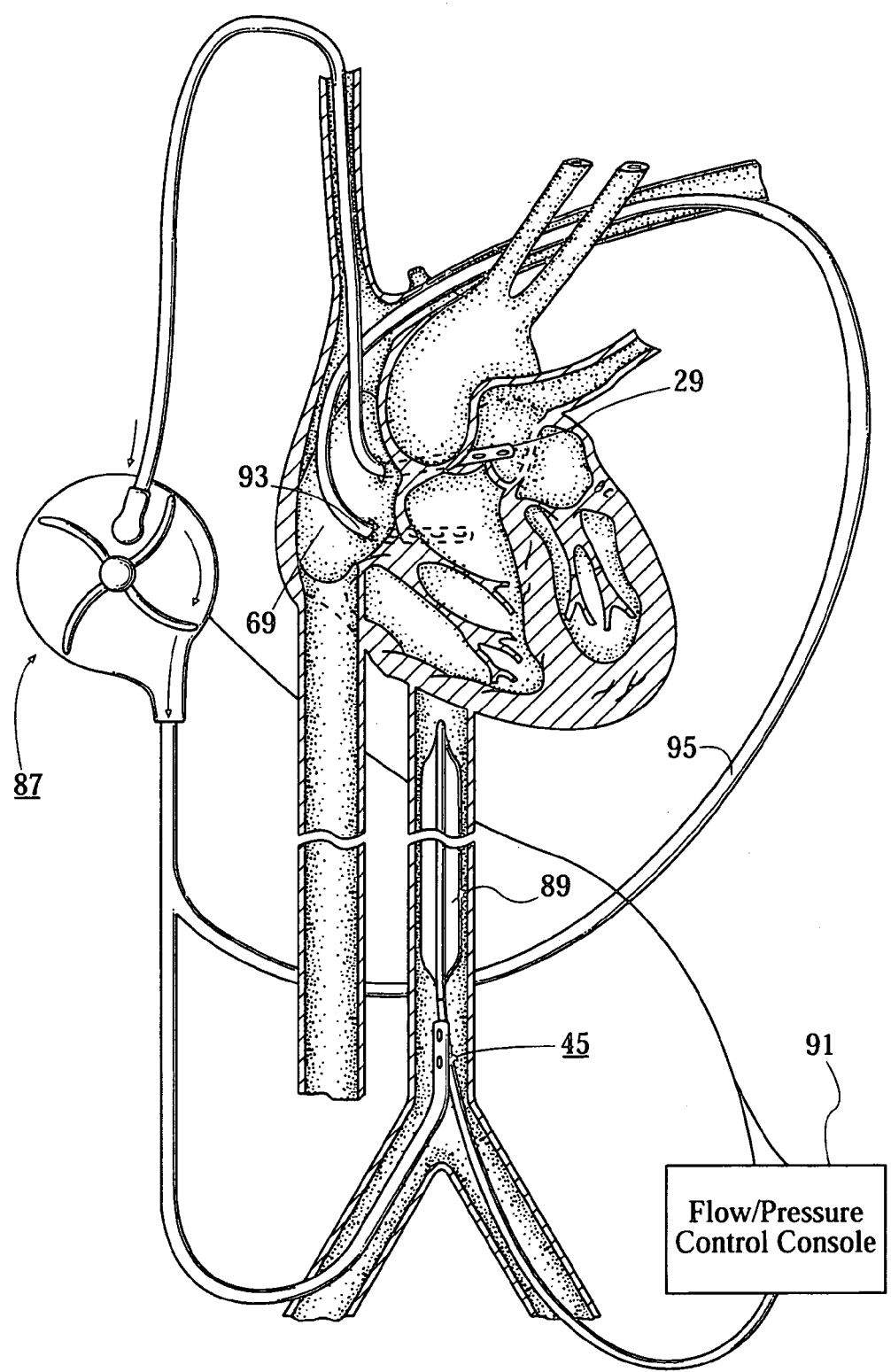
FIG. 10 is a view similar to FIG. 9 except that an intra-aortic balloon is also used.

FIG. 10 is similar to FIG. 9 except that an intra-aortic balloon 89 is also used and coupled to a MIVAT console 91. The MIVAT control console allows for accurate sychronization of the devices to the heart's normal pumping action using standard electrical or pressure inputs. Sychronization of the electrical stimulation or cardioversion of the heart and pumping action of pumping mechanism are fully integrated and managed with the MIVAT control console to ensure complete electromechanical integration and management can occur. Data gathered from the various devices is then fed into a central processor with proper algorhythms used to manage multiple device interactions and proper treatment regiments.

FIG. 11 again shows the SAM-CS in a "least aorta disruptive" placement such that the left heart chamber is accessed from the right side. The configuration is essentially the same as that shown in FIG. 3, except that a peristaltic pump 97 is used for continuous flow. The peristaltic pump 97 can also be equipped with solenoid valves that are used to build pressure and then open fully (always partially open to ensure no stagnation of blood occurs) and also to close to low volume flow quickly to create a continuous yet auasi-pulsatile flow pulse of blood.

Figure 11:
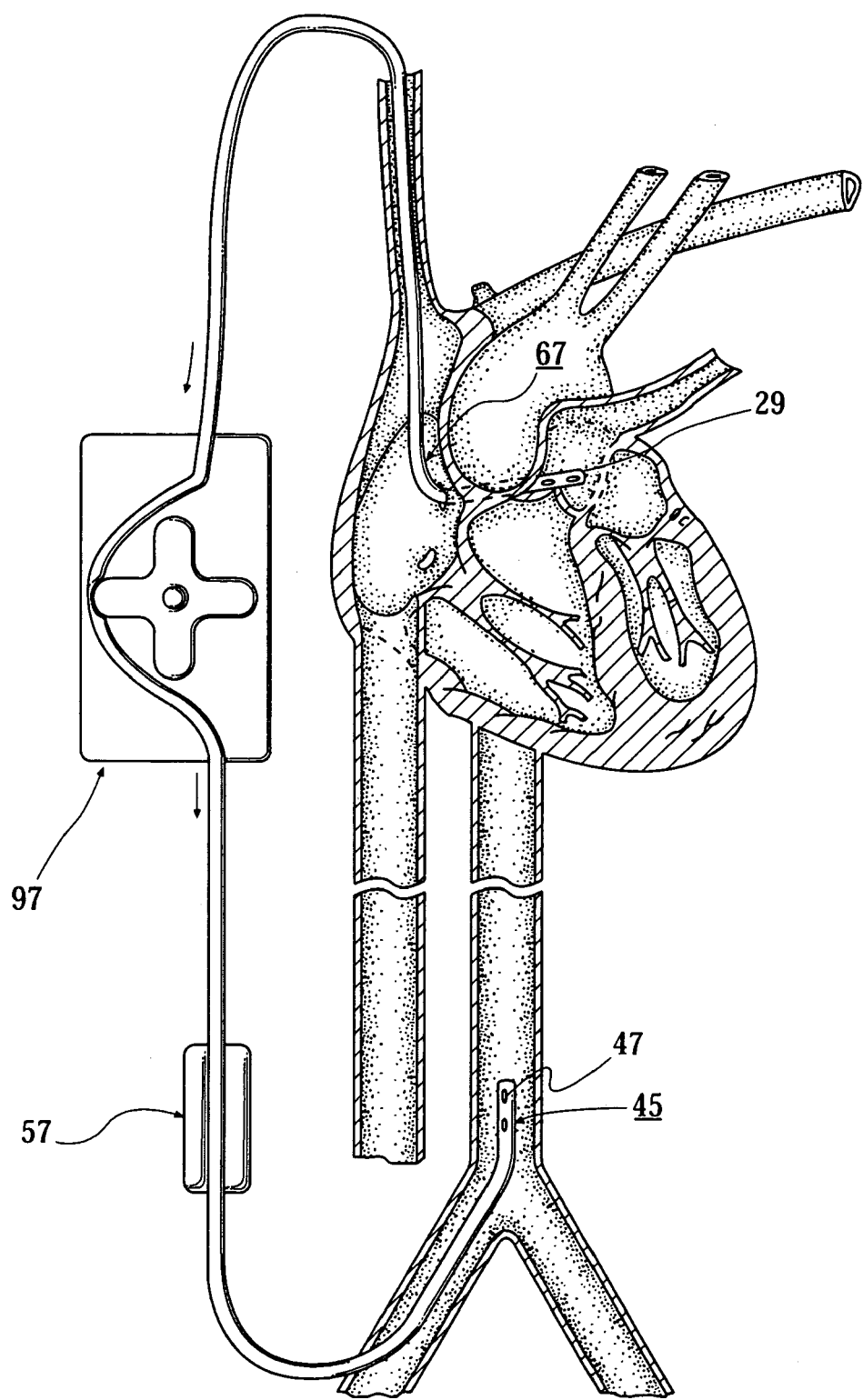
FIG. 11 is another view of the device of the invention in which a peristaltic pump is used for continuous flow.
Figure 12:
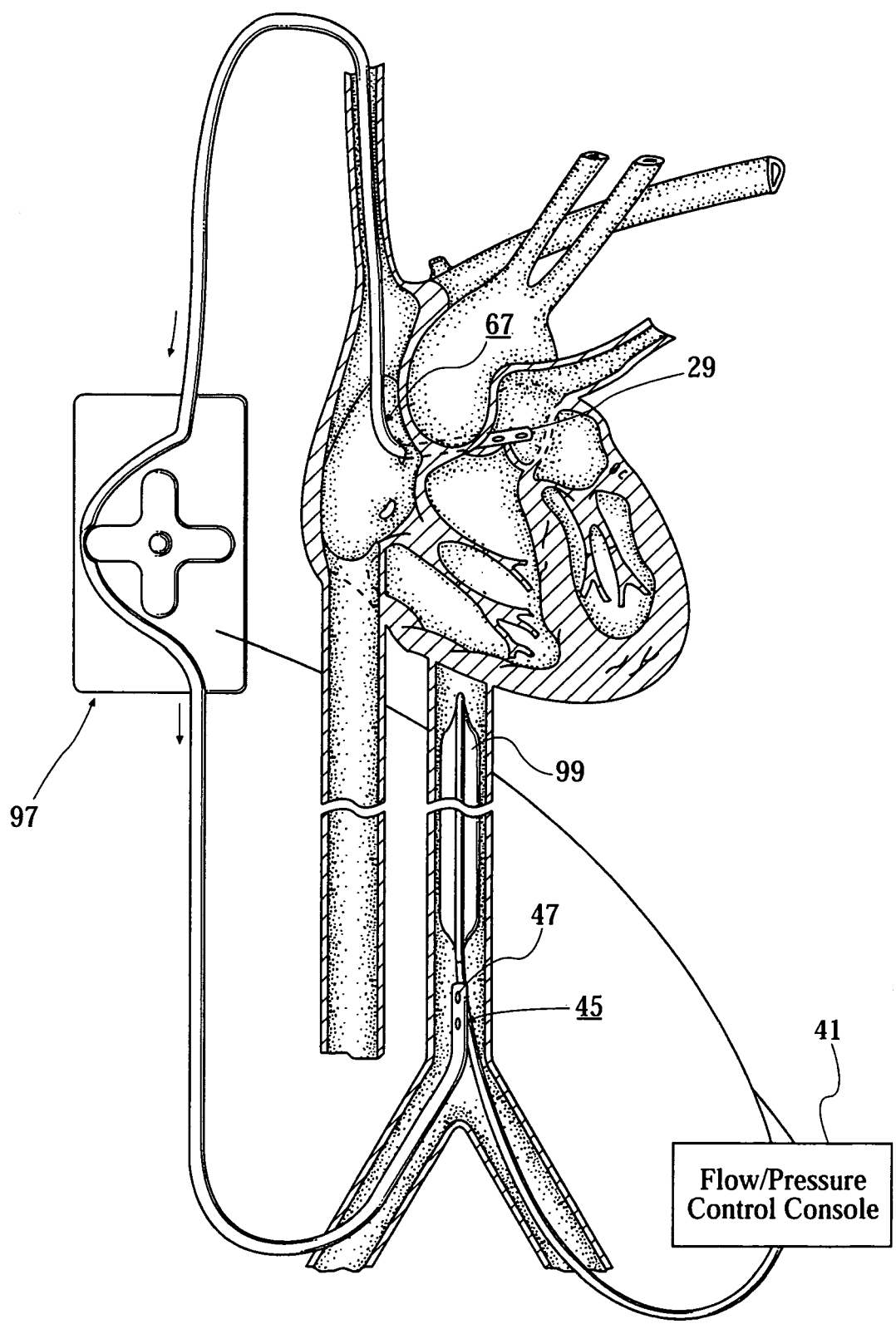
FIG. 12 is a view similar to FIG. 11 but showing the use of an intra-aortic balloon.

FIG. 12 is the same as FIG. 11 except that an intra-aortic balloon 99 is present and coupled to a MIVAT console. The MIVAT control console allows for accurate sychronization of the devices to the heart's normal pumping action using standard electrical or pressure inputs.

Figure 13:
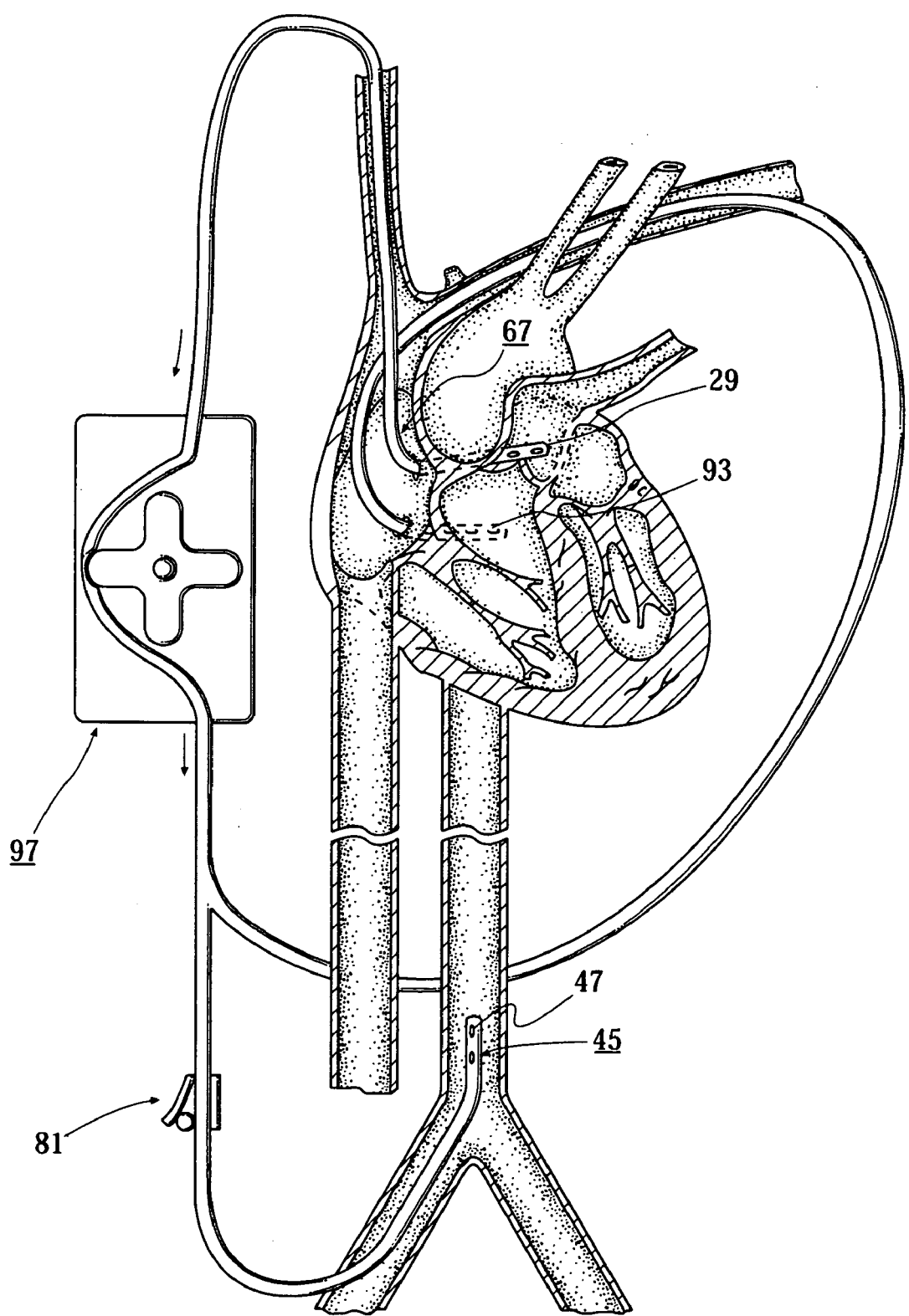
FIG. 13 is a view similar to FIG. 11 but with an additional cannula introduced into the coronary sinus.

FIG. 13 is the same as FIG. 12 except that an additional catheter is introduced into the coronary sinus and coupled to the MIVAT console. The Coronary Sinus cannula allows for retroperfusion of the myocardium through the veins branching from coronary sinus.

Figure 14:
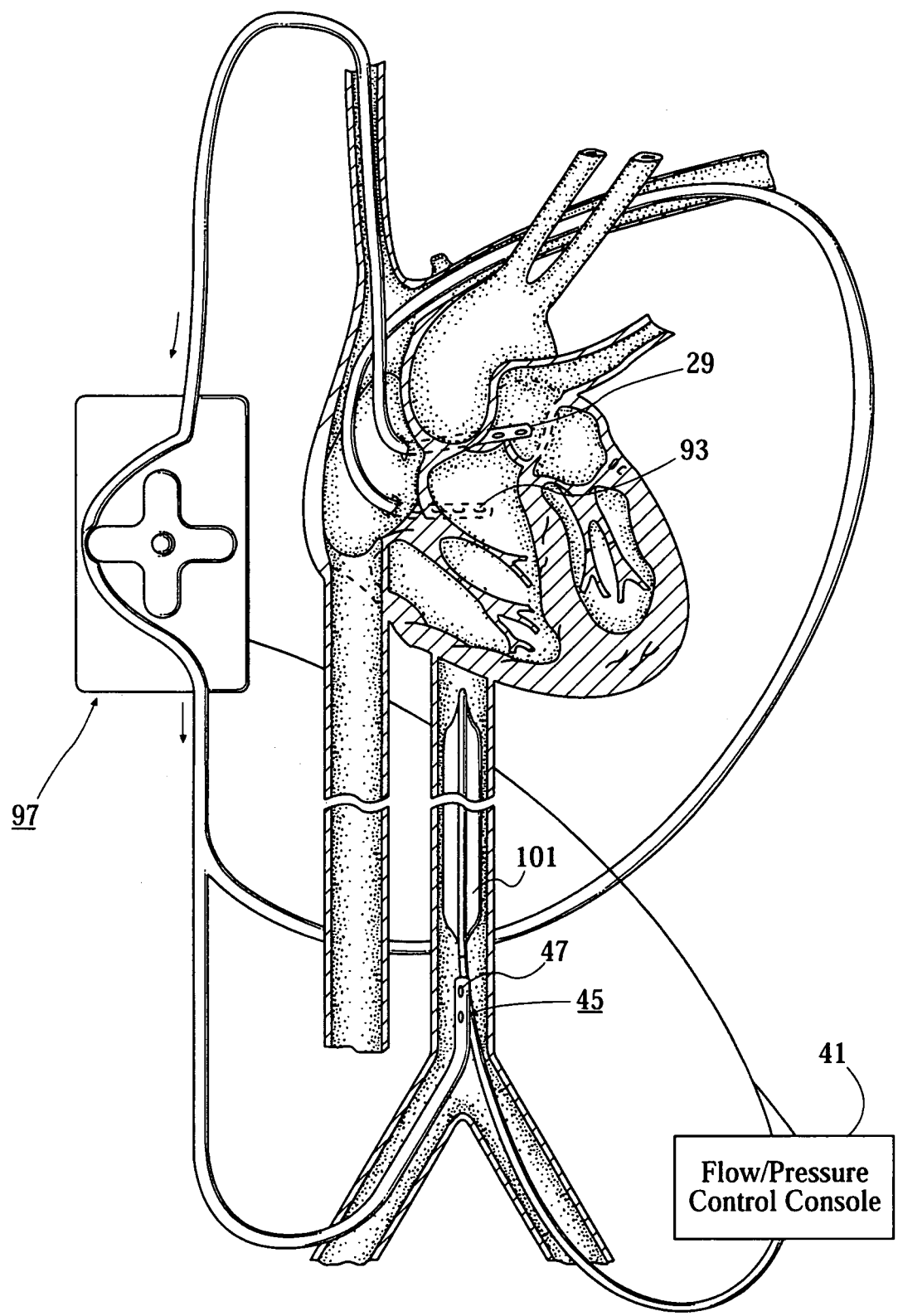
FIG. 14 is a view similar to FIG. 13 except that an intra-aortic balloon is also used.

FIG. 14 is the same as FIG. 13 except that an intra-aortic balloon 101 is also used and coupled to the MIVAT console.

Figure 15:
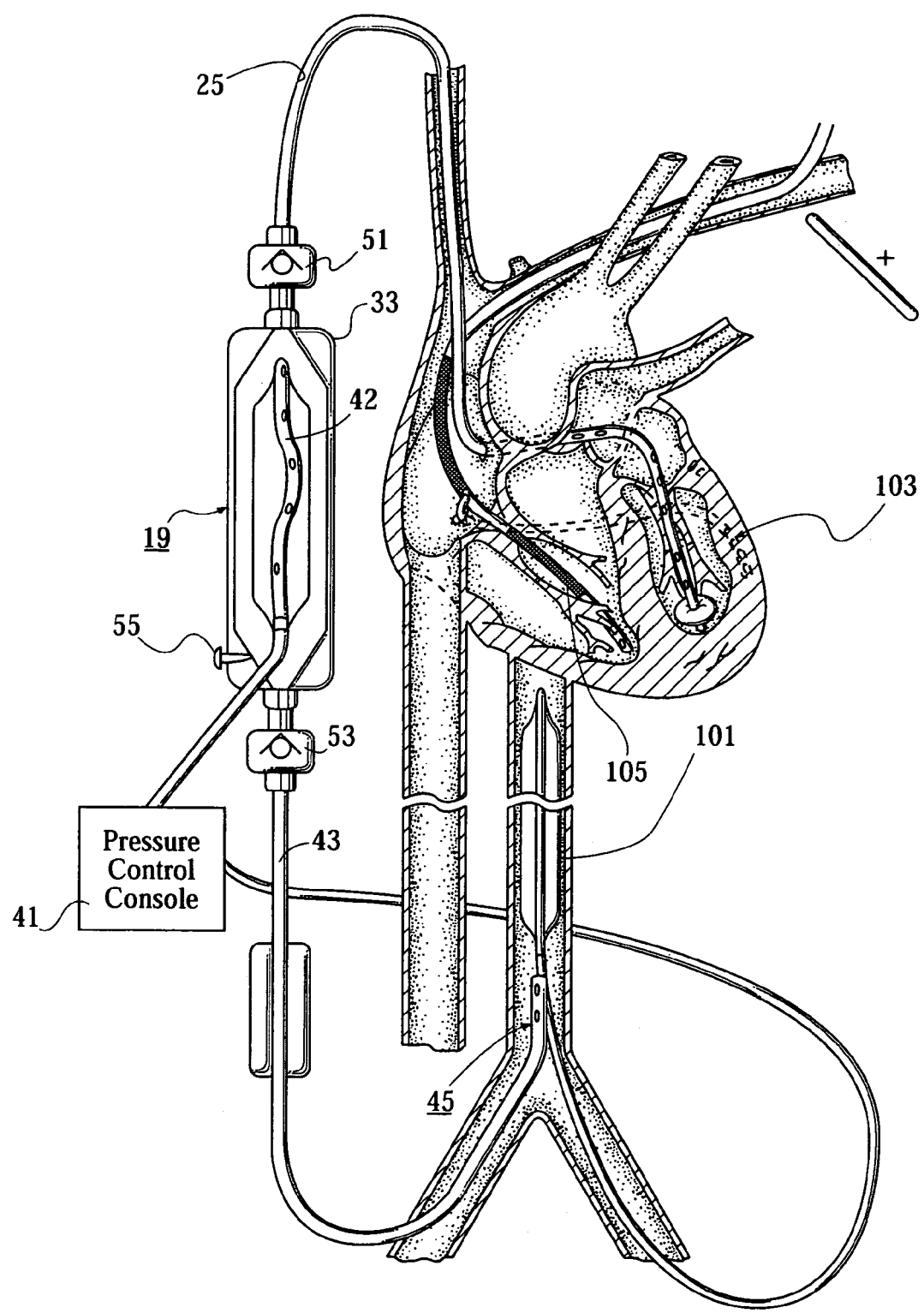
FIG. 15 is a view similar to FIG. 6 but with the addition of electrical catheters used to stimulate the heart.

FIG. 15 is similar to FIG. 14 but with the addition of electrical catheters 103, 105 used to stimulate the heart such that heart rate can be dictated by a pacing pulse. The design of the electrical catheter can be of the type know in the art as an ICD but being designed for temporary use such as detailed in U.S. Pat. No. 5,005,587. It is known in the relevant art to apply implanted cardioverting defibrillator technology to temporary catheters. The prior art also teaches the sensing of electrical signals within the heart, pacing within the heart, and also the internal cardioversion within the heart muscle, all done with a single device.

The present invention also envisions that the heart be equipped with a pacing/cardioversion catheter placed within the coronary sinus and extending into left cardiac vein. The electrical stimulation or cardioversion of the left and right ventricle can be achieved using a venous side access because both the anode and cathode reside in the venous system of the heart and optimize ventricular mass cattured. Prior art Diaz patent, U.S. Pat. No. 5,824,026, teaches that one or more pace/sense electrodes can be mounted onto a catheter having one or more cardioversion (HV) electrodes.

Figure 16:
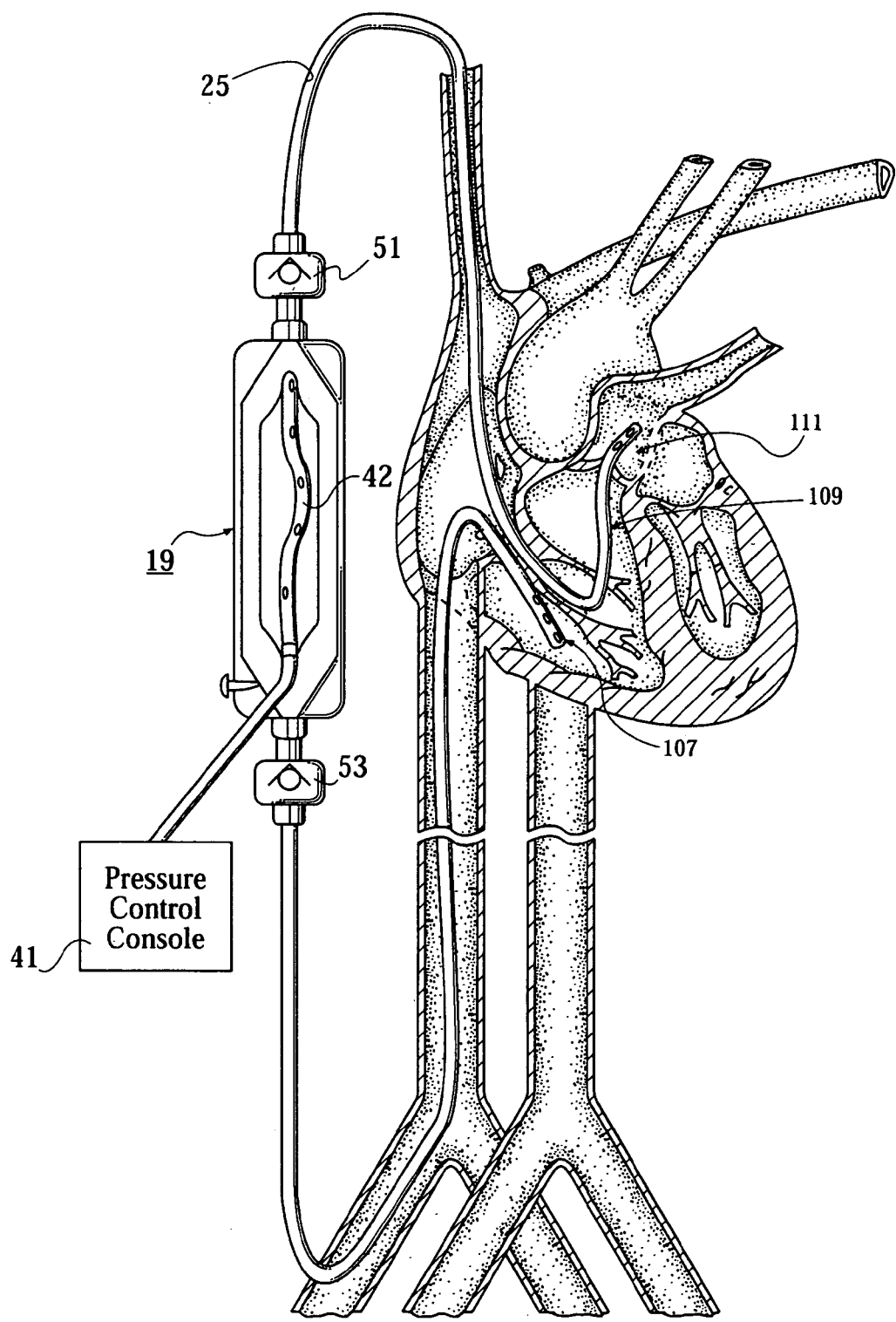
FIG. 16 is another embodiment of the device of the invention which shows the apparatus applied to the right side of the heart.

FIG. 16 shows the use of the same type apparatus as applied to the right side of the heart (venous side). A cannula 107 is placed within the right ventricle and is used to draw out blood from that ventricle. A second cannula 109 is placed within the pulmonary artery 111 and used to infuse blood within that artery. The pumping apparatuses described above can be used to achieve the necessary pumping and the sychronization can be accomplished using a MIVAT control console as previously described.

It is inherent in the disclosure of the present invention that a combination device might also be utilized that includes two independent SAM-CS's that are placed in least invasive locations of the body such that both the left and right ventricles are assisted. The MIVAT control console would be utilized for sychronizing the pumping action of both devices in synchrony with heart beat.

Figure 17:
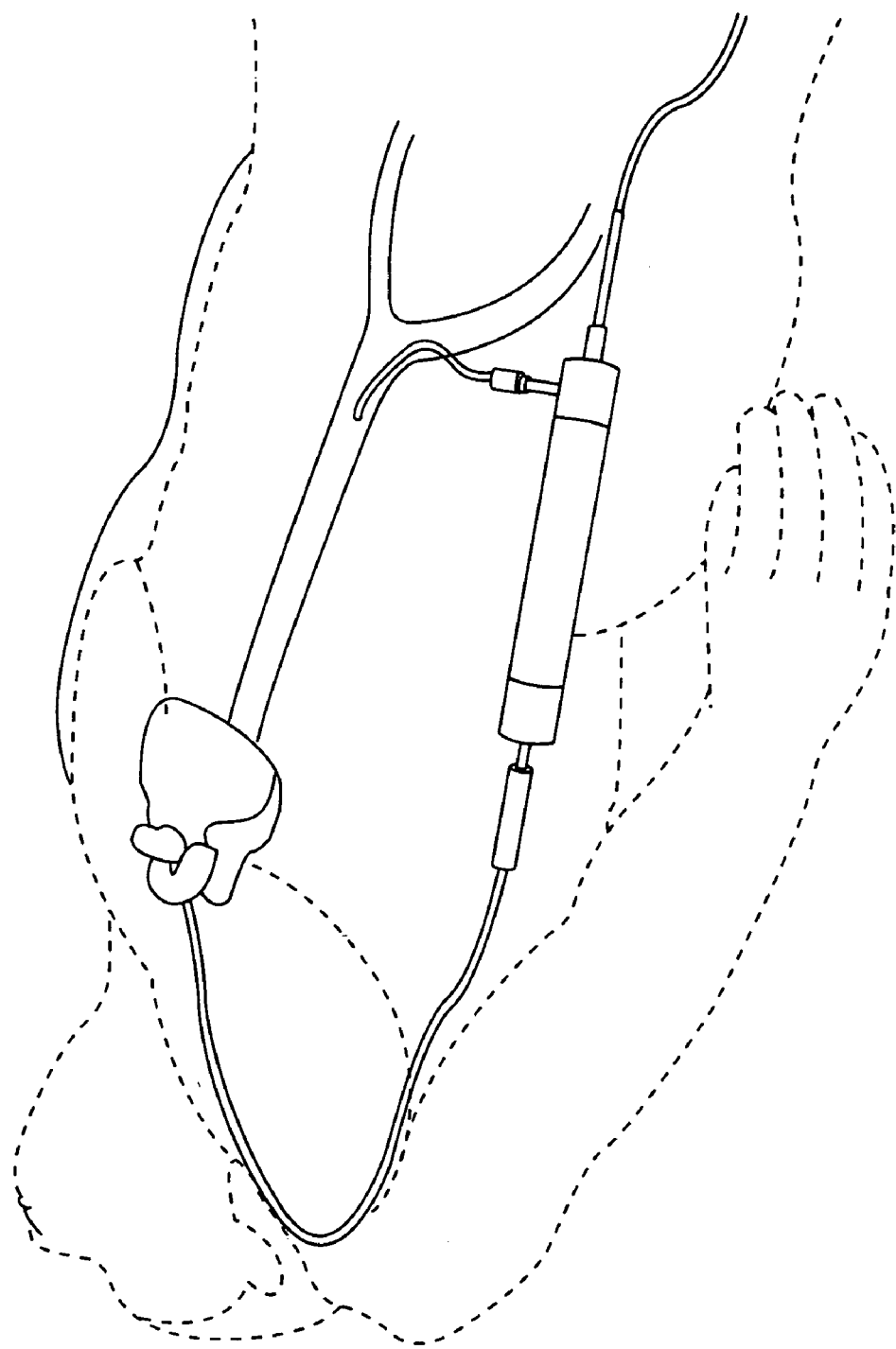
FIG. 17 shows one embodiment of the invention as it may be applied to a human model that also includes the internal devices of the invention as well as other supplemental devices connected to the patient.

FIG. 17 shows one embodiment of the invention as it may be applied to the human model and includes the internal devices as well as other supplemental devices that connect to patient. FIG. 17 shows a patient using the transeptal approach to gain access to left chambers of heart.

Figure 18:
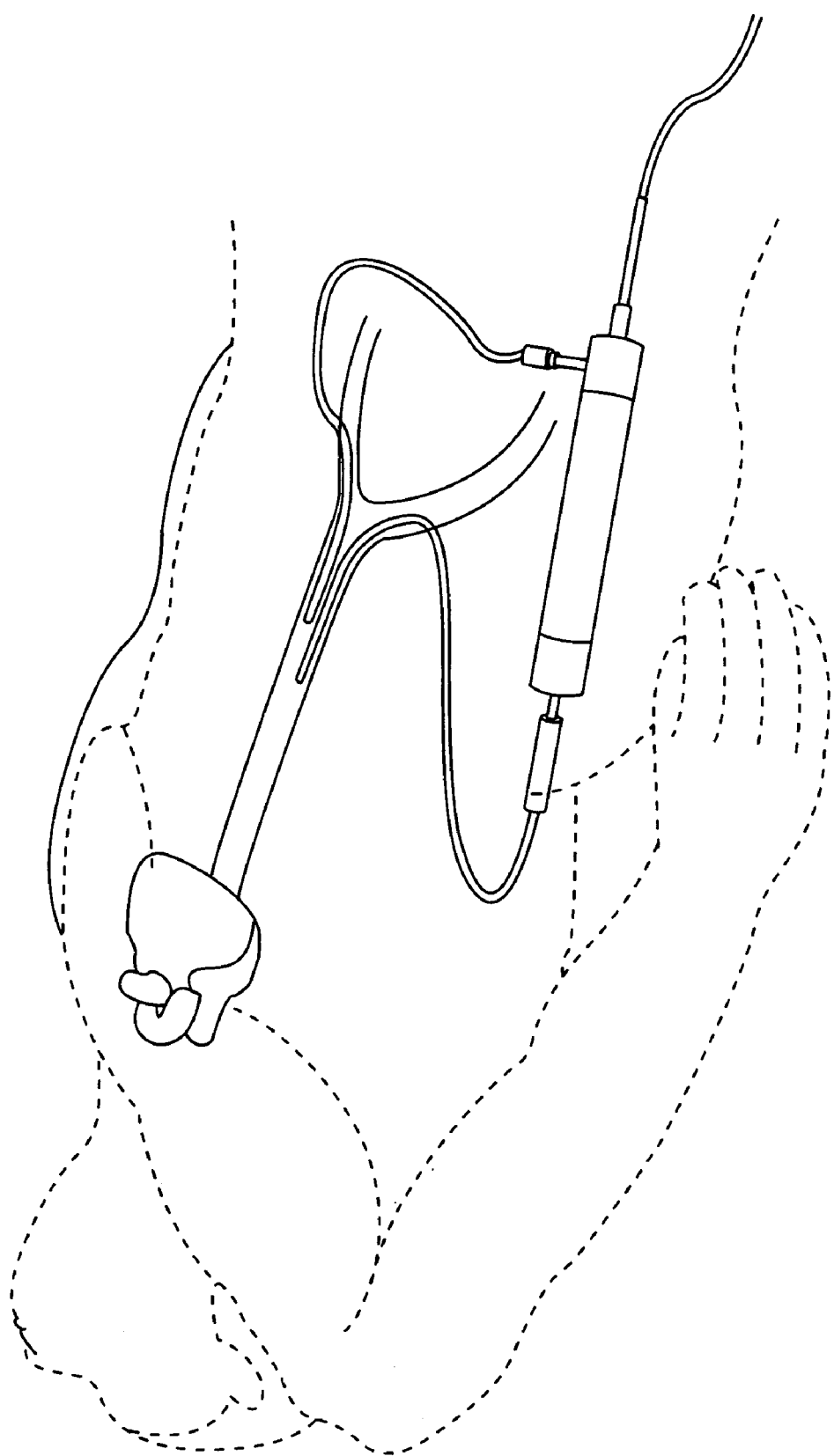
FIG. 18 is another view, similar to FIG. 17, showing the placement of the device of the invention on a human model.

FIG. 18 is a similar view which shows an inferior only approach whereby the cut down or percutaneous puncture occurs in the patient's legs. One cannula draws blood and the second infuses blood back into aorta.

Figure 19:
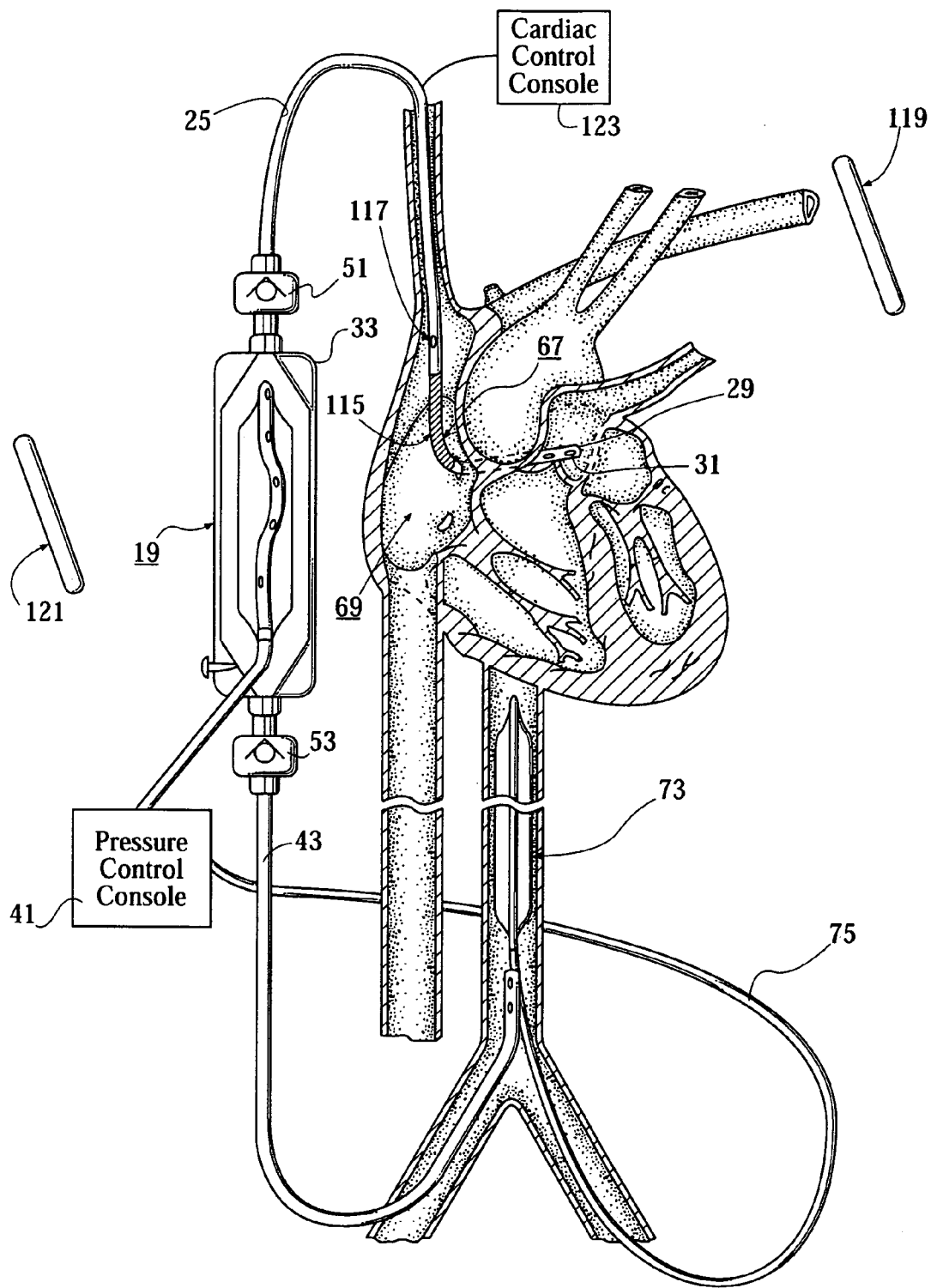
FIG. 19 is another view similar to FIG. 6 but with the addition of electrically active regions having sensing and cardioversion electrodes integrated into the transeptal tube or sheath.

FIG. 19 is another view similar to FIG. 6 but with the addition of an electrically active region 115 having sensing, and cardioversion electrodes integrated into the transeptal tube (sheath) such that the "p" segments of the pQRSt electrical signal attained inside the heart can be used to trigger the pump. In the particular embodiment of FIG. 19, a second electrode area 117 is located on the tube. The electrodes located on the sheath are ideally positioned within the right atrium such that atrial pacing and or cardioversion of AF (Atrial Fibrillation or Atrial Flutter) or AT (Atrial Tachycardia) can be achieved between the electrodes on the tube or sheath or by incorporating the cutaneous pad or pads (119, 121 in FIG. 19) onto the back or chest of the patient. Electrical synchronization is achieved by means of an electrical connection 123 to the control console, as described above.

Figure 20:
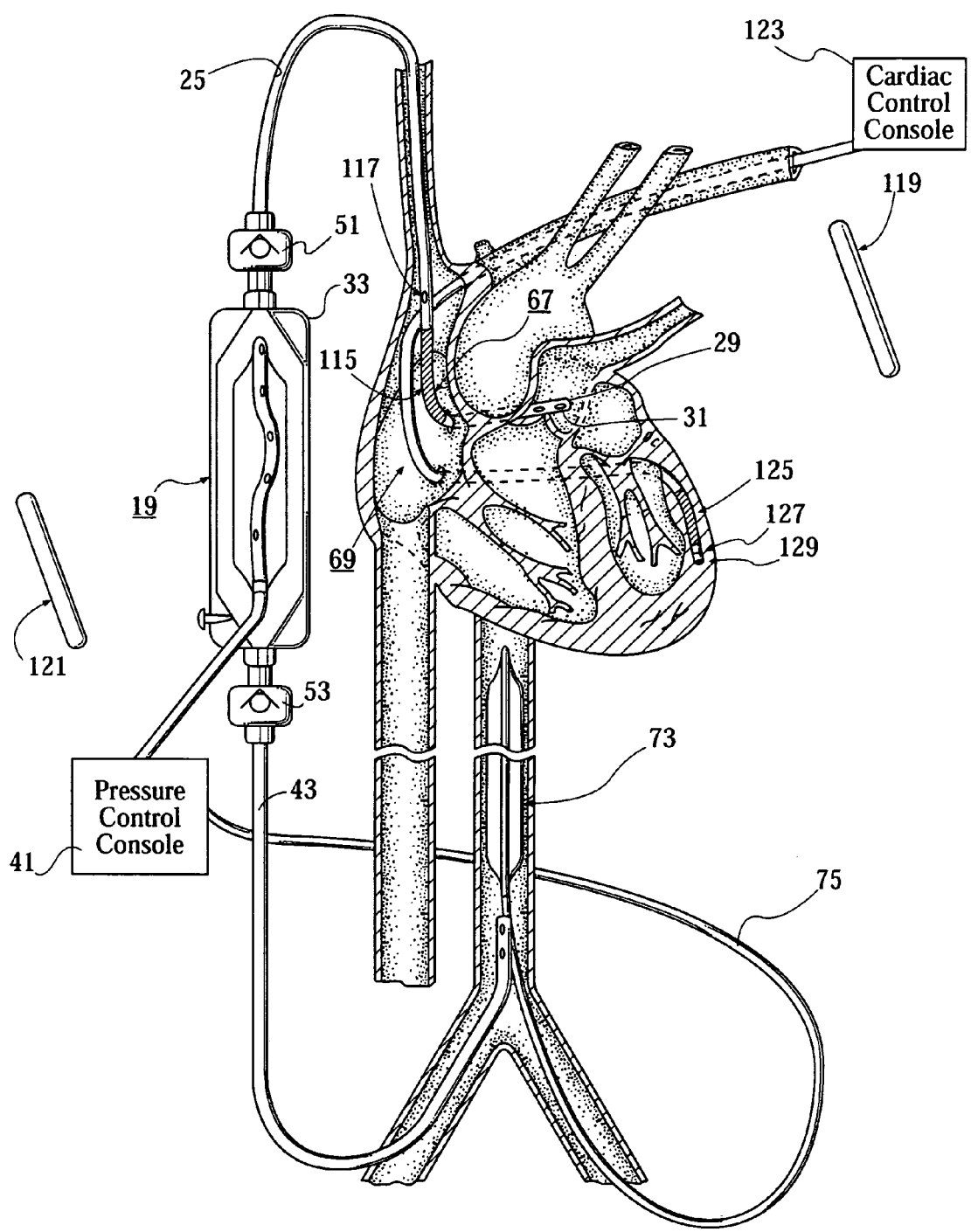
FIG. 20 is another view similar to FIG. 19 but with the addition of a catheter located in the cardiac vein.

FIG. 20 is another view similar to FIG. 19 but with the addition of a catheter 125 located in the cardiac vein such that a shock vector between the catheter in the cardiac vein and the electrically active region 115 on the tube or sheath can be used to terminate Ventricular Tachycardia (VT) and or Ventricular Flutter (VF). The use of cutaneous pads 119, 121 can also be incorporated to form a second multi-directional shock field that can be characterized by shock vectors that form a three dimensional energy field to terminate difficult to terminate VT or VF. The choice of the number of active vectors and or creation of vector or field can be controlled by means incorporated into the cardiac control console 123. The particular catheter 125 in FIG. 20 also incorporates a pair of pacing electrodes 127, 129 for left ventricle pacing.

ADVANTAGES. The devices of the invention are relatively simple in design and economical to manufacture and additionally the devices work in harmony to compliment existing therapeutic procedures. The devices serve to limit the energy expensive component of internal work during cardiac contraction, so that under conditions of limited availability of cardiac energy, more of the energy can be devoted to the external work of pumping blood. The devices of the invention serve to reduce coronary pressure during the contraction phase of the cardiac cycle and also increase coronary pressure during the relaxation phase, when the coronary flow normally nourishes the heart muscle. The increase in coronary flow during the relaxation phase of the cardiac cycle serves to increase flow through primary as well as supplemental, i.e., collateral blood vessels supplying tissue whose normal source of blood flow has been compromised by coronary artery disease or other causes. The increase in coronary pressure during the relaxation phase of the heart cycle is particularly beneficial in cases of limited cardiac contractile function due to inadequate coronary blood flow or to conditions which limit the production of metabolic energy for cardiac work. The use of the proposed devices and techniques of the invention should decrease cardiac morbidity and mortality, thereby saving lives.

While the invention has been shown in several of its forms, it is not thus limited but is susceptible to various changes and modifications without departing from the spirit thereof.

What is claimed is:

1. A minimally invasive technique for improving blood flow in a patient's body by removing blood directly or indirectly from a selected ventricle of the heart and then directly or indirectly infusing the blood back into the patient's circulatory system at a selected distant location, the technique comprising the steps of:

installing a flexible catheter having a length, an open interior, an exposed proximate end and a distal end within the patient's left ventricle by means of a transeptal puncture of the patient's right atrium, the catheter having at least one opening along the length of the said flexible tube for admitting blood into the open interior after the catheter has been installed;

providing an electrically active region having sensing, pacing and cardioversion electrodes integrated into the flexible catheter, the electrodes being positioned within the patient's right atrium;

achieving atrial pacing and/or cardioversion of atrial fibrillation or atrial tachycardia by electrical conduction between the electrodes on the flexible catheter or between a selected electrode on the flexible catheter and an external cutaneous pad on the patient's body;

providing a supplemental assist mechanism located externally of a patient's body and connected to the proximate end of the flexible catheter, the supplemental assist mechanism comprising a rigid housing with an inlet and an outlet and with a housing interior in communication with the flexible catheter for receiving blood from the arterial circulation, the rigid housing also having a pumping membrane located within the housing interior;

connecting a flexible cannula to the outlet of the rigid housing, the cannula having a distal end with an end opening which is located within the patient's body at a selected location distant from the ventricle for reinfusing blood at the selected distant location;

providing a control console having at least two independent control channels for alternately supplying vacuum and pressure to the pumping membrane, the application of vacuum to the membrane causing the membrane to collapse and causing blood to be drawn into the housing interior from the ventricle, the application of pressure to the membrane causing the membrane to inflate and act against blood in the housing interior to drive blood from the housing interior into the patient's body at the selected distant location.

2. The minimally invasive technique of claim 1, further comprising the step of:

providing a synchronizing means as a part of the control console for varying the membrane inflation and deflation in synchrony with the cardiac cycle of a patient being treated with the device.

3. The minimally invasive technique of claim 1, further comprising the steps of:

locating an additional electrically active catheter within the patient's cardiac vein such that a shock vector produced between the additional electrically active catheter in the cardiac vein and the electrically active region on the flexible catheter can be used to terminate ventricular tachycardia and/or ventricular flutter.

4. The minimally invasive technique of claim 3, further comprising the use of external cutaneous pads to form a multi-directional shock field that can be characterized by shock vectors that form a three dimensional energy field within the patient's body to terminate difficult to terminate ventricular tachycardia or ventricular flutter.

* * * * *